United States Patent [19]

Tomioka et al.

[11] Patent Number: 5,756,522

[45] Date of Patent: May 26, 1998

[54] TRIAZOLE DERIVATIVES AND USES THEREOF

[75] Inventors: Hiroki Tomioka, Ikeda; Takashi Furukawa; Yoji Takada, both of Toyonaka; Hirotaka Takano, Sanda, all of Japan

[73] Assignee: Sumitomo Chemical Company, Limited, Osaka, Japan

[21] Appl. No.: 772,086

[22] Filed: Dec. 20, 1996

[30] Foreign Application Priority Data

Dec. 21, 1995 [JP] Japan ................ 7-333463
Oct. 1, 1996 [JP] Japan ................ 8-260917

[51] Int. Cl.$^6$ ............ A61K 31/44; A61K 31/41; C07D 401/04; C07D 249/12
[52] U.S. Cl. ............ 514/340; 514/183; 514/210; 514/236.2; 514/227.8; 514/365; 514/374; 514/384; 544/60; 544/132; 546/272.4; 548/146; 548/214; 548/263.8; 548/264.2; 548/950; 548/962
[58] Field of Search ............ 548/263.8, 264.2, 548/146, 214, 962, 950; 514/384, 340, 365, 374, 227.8, 236.2, 183, 210; 546/272.4; 544/60, 132

[56] References Cited

U.S. PATENT DOCUMENTS

| | | | |
|---|---|---|---|
| 4,925,864 | 5/1990 | Inamori et al. | 514/383 |
| 4,957,935 | 9/1990 | Inamori et al. | 514/383 |
| 5,109,004 | 4/1992 | Bettesworth et al. | 514/269 |

FOREIGN PATENT DOCUMENTS

| | | |
|---|---|---|
| 0 285 893 A2 | 10/1988 | European Pat. Off. |
| 43 43 528 A1 | 6/1995 | Germany |
| 2-42423 | 2/1990 | Japan |
| 2-91061 | 3/1990 | Japan |
| 2-91062 | 3/1990 | Japan |
| 7-258227 | 10/1995 | Japan |

*Primary Examiner*—Joseph McKane
*Attorney, Agent, or Firm*—Birch, Stewart, Kolasch & Birch, LLP

[57] ABSTRACT

Disclosed are triazole derivatives represented by the following formula, insecticides and acaricides containing the triazole derivatives as active ingredients, and a method of controlling insect pests and mites.

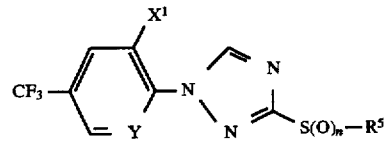

wherein $R^1$ represents a hydrogen atom, a lower alkyl group, a halogen atom, 1-pyrrolyl group, a group represented by the formula $NR^2R^3$; $R^5$ represents a methyl or ethyl group substituted with at least one halogen atom; n represents 0, 1 or 2; Y represents a nitrogen atom or a group represented by the formula $CX^2$; and $X^1$ and $X^2$ are the same or different and each represent a halogen atom, a nitro group or a cyano group.

16 Claims, No Drawings

TRIAZOLE DERIVATIVES AND USES THEREOF

BACKGROUND OF THE INVENTION

The present invention relates to triazole derivatives and uses thereof.

It is disclosed in JP-A-1-230562 and JP-A-2-91061 that some triazole derivatives can be used as active ingredients of insecticides.

However, these compounds are not necessarily sufficient as active ingredients of insecticides in insecticidal efficacy.

The present inventors have made intensive studies in an attempt to find compounds having excellent insecticidal efficacy and, as a result, have found that triazole derivatives represented by the following formula have an excellent insecticidal and acaricidal efficacy. Thus, the present invention has been accomplished.

SUMMARY OF THE INVENTION

That is, the present invention provides a triazole derivative represented by the following formula [1] (hereinafter referred to as "the present compound" and insecticides and acaricides containing the triazole derivative as an active ingredient:

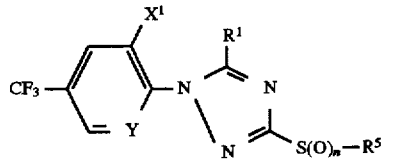

{wherein $R^1$ represents a hydrogen atom, a lower alkyl group (for example, a $C_1$–$C_4$ alkyl group such as methyl group and ethyl group, a halogen atom (for example, fluorine atom, chlorine atom, bromine atom or the like), 1-pyrrolyl group, a group represented by the formula $NR^2R^3$ [where $R^2$ and $R^3$ are the same or different and each represent a hydrogen atom, an alkyl group (for example, a $C_1$–$C_8$ alkyl group such as methyl, ethyl, propyl, isopropyl, butyl, isobutyl, sec-butyl, tert-butyl and neopentyl group), a cycloalkyl group (for example, a $C_3$–$C_8$ cycloalkyl group such as cyclopropyl, cyclobutyl, cyclopentyl and cyclohexyl group), an alkoxyalkyl group (for example, a ($C_1$–$C_8$ alkoxy) $C_1$–$C_8$ alkyl group such as methoxymethyl, ethoxymethyl, propoxymethyl, isopropoxymethyl, butoxymethyl, isobutoxymethyl, sec-butoxymethyl, 2-methoxyethyl, 1-methoxy-2,2-dimethylpropyl, 1-ethoxy-2,2-dimethylpropyl, 1-methoxy-1,2,2-trimethylpropyl and 1-ethoxy-1,2,2-trimethylpropyl group), an alkylthiocarbonyl group (for example, $C_2$–$C_5$ alkylthiocarbonyl group such as ethylthiocarbonyl, methylthiocarbonyl, isopropylthiocarbonyl, butylthiocarbonyl group), an alkoxycarbonylsulfenyl group (for example, $C_2$–$C_5$ alkoxycarbonylsulfenyl group such as methoxycarbonylsulfenyl, ethoxycarbonylsulfenyl, isopropoxycarbonylsulfenyl and butoxycarbonylsulfenyl group), an alkylthio group (for example, $C_1$–$C_4$ alkylthio group such as butylthio, isopropylthio, tert-butylthio, ethylthio and propylthio group), an alkylsulfonyl group (for example, $C_1$–$C_4$ alkylsulfonyl group such as methanesulfonyl, ethanesulfonyl and butanesulfonyl group), a substituted phenyl group (for example, 2,6-dichloro-4-trifluoromethylphenyl, 2-chloro-4-nitro-5-trifluoromethylphenyl, 3-chloro-6-nitro-4-trifluoromethylphenyl and 3-chloro-2,6-dinitro-4-trifluoromethylphenyl group), an alkylthioalkyl group (for example, a ($C_1$–$C_8$ alkylthio) $C_1$–$C_8$ alkyl group such as methylthiomethyl, ethylthiomethyl, propylthiomethyl, isopropylthiomethyl, butylthiomethyl, isobutylthiomethyl, sec-butylthiomethyl, 2-methylthioethyl, 1-methylthio-2,2-dimethylpropyl, 1-ethylthio-2,2-dimethylpropyl, 1-methylthio-1,2,2-trimethylpropyl and 1-ethylthio-1,2,2-trimethylpropyl group), an alkoxycarbonyl group (for example, a ($C_1$–$C_8$ alkoxy)-carbonyl group such as methoxycarbonyl and ethoxycarbonyl group), an unsubstituted or alkoxy-substituted alkanoyl group (for example, a $C_2$–$C_8$ alkanoyl group such as acetyl, propanoyl, butanoyl, 3-methylbutanoyl, 2-methylpropanoyl and pentanoyl group, a $C_3$–$C_6$ alkoxy-substituted alkanoyl group such as methoxyacetyl, ethoxyacetyl, propoxyacetyl, isopropoxyacetyl and butoxyacetyl group) or a saturated heterocyclic ring (for example, 2-tetrahydropyranyl group), or the formula

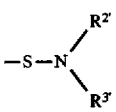

[wherein $R^{2'}$ and $R^{3'}$ are the same or different and each represent an alkyl group (for example, a $C_1$–$C_4$ alkyl group such as methyl, ethyl, propyl, isopropyl, butyl, isobutyl, sec-butyl and tert-butyl group), an alkoxycarbonyl group (for example, an $C_2$–$C_5$ alkoxycarbonyl group such as methoxycarbonyl, ethoxycarbonyl and butoxycarbonyl group), an alkoxycarbonyl-substituted alkyl group (for example, an $C_4$–$C_7$ alkoxycarbonyl-substituted alkyl group such as, 2-methoxycarbonylethyl, 2-ethoxycarbonylethyl and 2-butoxycarbonyl ethyl group), or $R^{2'}$ and $R^{3'}$ link to each other to form an oxygen-containing alkylene group (for example, $CH_2CH_2OCH_2CH_2$) or $R^2$ and $R^3$ represent a nitrogen-containing saturated heterocyclic ring which may be substituted or a pyrrolyl group in combination with nitrogen atom to which they bond] or a group represented by the formula $N=CR^4R^6$ [where $R^4$ represents a hydrogen atom, an alkyl group (for example, a $C_1$–$C_8$ alkyl group such as methyl, ethyl, propyl, isopropyl, butyl, isobutyl, sec-butyl and tert-butyl group) or an unsubstituted or substituted phenyl group and $R^6$ represents a hydrogen atom, an alkyl group (for example, a $C_1$–$C_8$ alkyl group such as methyl, ethyl, propyl, isopropyl, butyl, isobutyl, sec-butyl or tert-butyl group), an alkoxy group (for example, a $C_1$–$C_8$ alkoxy group such as methoxy and ethoxy group) or a dialkylamino group (for example, a $C_1$–$C_8$ dialkylamino group such as dimethylamino or diethylamino group)]; $R^5$ represents a methyl group substituted with at least one halogen atom such as fluorine, chlorine and bromine atom (for example, trifluoromethyl, difluoromethyl, chlorodifluoromethyl or bromodifluoromethyl group) or an ethyl group substituted with at least one halogen atom such as fluorine, chlorine and bromine atom (for example, 1,1,2,2-tetrafluoroethyl, 2,2,2-trifluoroethyl, pentafluoroethyl, 1,1-difluoroethyl or 2-bromo-1,1,2,2-tetrafluoroethyl group); n represents 0, 1 or 2; Y represents a nitrogen atom or a group represented by the formula $CX^2$; and $X^1$ and $X^2$ are the same or different and each represent a halogen atom (for example, chlorine, bromine or fluorine atom), a nitro group or a cyano group}. The present invention further provides insecticide and/or acaricides containing the above triazole derivative as an active ingredient.

DESCRIPTION OF THE INVENTION

As the substituents in the case that $NR^2R^3$ represents a nitrogen-containing saturated heterocyclic ring which may be substituented, mention may be made of, for example, an alkyl group (for example, a $C_1$-$C_4$ alkyl group such as methyl, ethyl, propyl, isopropyl, butyl, isobutyl, sec-butyl and tert-butyl group), a halogen atom (for example, fluorine, chlorine or bromine atom), an alkoxy group (for example, a $C_1$-$C_4$ alkoxy group such as methoxy and ethoxy group), a hydroxyl group, a mercapto group, an alkoxycarbonyl group (for example, a ($C_1$-$C_4$ alkoxy)carbonyl group such as methoxycarbonyl and ethoxycarbonyl group), an oxo group or an acyloxy group (for example, a $C_1$-$C_{10}$ acyloxy group such as acetoxy, pivaloyloxy and benzoyloxy group).

As the saturated heterocyclic ring in the case that $NR^2R^3$ represents a nitrogen-containing saturated heterocyclic ring which may be substituted, mention may be made of, for example, 3-membered or 4-membered saturated heterocyclic rings such as aziridine ring and azetidine ring and 5-membered or 6-membered saturated heterocyclic rings which may contain an oxygen atom or a sulfur atom in addition to the nitrogen atom, such as pyrrolidine ring, morpholine ring, thiomorpholine ring, isothiazolidine ring, 1,3-oxazolidine ring and 1,3-thiazolidine ring.

As the substituents in the substituted phenyl group represented by $R^2$, $R^3$ or $R^4$, mention may be made of, for example, a hydroxyl group, an alkoxy group (for example, a $C_1$-$C_4$ alkoxy group such as methoxy and ethoxy group), an alkyl group (for example, a $C_1$-$C_4$ alkyl group such as methyl and ethyl group), a nitro group, a halogen atom (for example, fluorine, chlorine or bromine atom), a phenyl group, a phenoxy group, an alkylthio group (for example, a $C_1$-$C_4$ alkylthio group such as methylthio and ethylthio group), an amino group, a carboxyl group, a cyano group, an alkoxycarbonyl group (for example, a ($C_1$-$C_4$ alkoxy)carbonyl group such as methoxycarbonyl and ethoxycarbonyl group), and an acyloxy group (for example, a $C_1$-$C_{10}$ acyloxy group such as acetoxy, pivaloyloxy and benzoyloxy group).

In the present invention, $R^1$ is preferably hydrogen atom, methyl group or a group represented by $NR^2R^3$, and $R^2$ and $R^3$ are preferably hydrogen atom, an alkoxycarbonyl group or an alkanoyl group for $R^2$ and hydrogen atom, alkyl group, cycloalkyl group, alkoxycarbonyl group, alkoxycarbonylsulfenyl group, alkoxyalkyl group or the formula

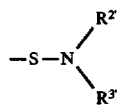

for $R^3$. $R^5$ is preferably a group represented by the formula $CF_2Z$ [where Z represents a halogen atom (for example, fluorine, chlorine or bromine atom), a hydrogen atom, a methyl group, a difluoromethyl group, a trifluoromethyl group or a bromodifluoromethyl group]. Y is preferably a group represented by the formula $CX^2$.

The process for preparation of the present compound will be explained in detail below. The present compound can be prepared, for example, by the following (process 1)–(process 10).

(Process 1)

(Process for the preparation of the present compound represented by the formula [1] where n is 0):

The present compound where n is 0 can be prepared by reacting a disulfide compound represented by the formula [2]:

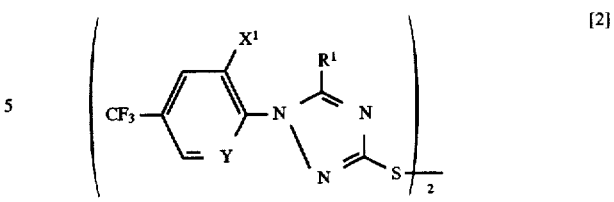

[wherein $R^1$, $X^1$ and Y are as defined above] with a halide compound represented by the formula [3]:

$$Z^1 - R^5 \quad [3]$$

[wherein $R^5$ is as defined above and $Z^1$ represents a bromine atom or an iodine atom] in the presence of a reducing agent.

Examples of the halide compound [3] are iodotrifluoromethane, bromotrifluoromethane, dibromodifluoromethane, bromochlorodifluoromethane, iodopentafluoroethane and iodotetrafluoroethane.

Examples of the reducing agent used are hydroxymethanesulfinates formed with various cations (for example, alkali metal hydroxymethanesulfinates such as sodium hydroxymethanesulfinate) and alkali metal dithionites (for example, sodium dithionite).

As for the amounts of the reactants, generally, the halide compound [3] is used in an amount of 2–3 mols and the reducing agent is used in an amount of 2–6 mols for 1 mol of the disulfide compound [2].

This reaction is carried out usually at a temperature in the range of about −20° C. to 150° C. for about 1–24 hours in a solvent, if necessary, in a pressure vessel.

As examples of the solvent used, mention may be made of aliphatic hydrocarbon solvents such as hexane, heptane, ligroin and petroleum ether; aromatic hydrocarbon solvents such as benzene, toluene and xylene; halogenated hydrocarbon solvents such as dichloroethane, chlorobenzene and dichlorobenzene; ketone solvents such as acetone, methyl ethyl ketone, methyl isobutyl ketone, isophorone and cyclohexanone; ester solvents such as ethyl acetate and butyl acetate, solvents such as acetonitrile and isobutyronitrile nitrile; acid amides such as formamide, N,N-dimethylformamide and N,N-dimethylacetamide; sulfur compounds such as dimethyl sulfoxide and sulfolane; water; and mixtures thereof.

After the completion of the reaction, the desired present compound can be isolated by carrying out usual aftertreatments such as extraction with organic solvents and concentration. If necessary, the product can be further purified by chromatography, distillation, recrystallization or the like.

(Process 2)

(Process for the preparation of the present compound represented by the formula [1] where n is 0):

The present compound where n is 0 can be prepared by reacting a mercaptan represented by the formula [4]:

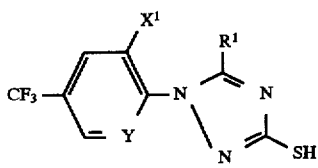

[where $R^1$, $X^1$ and Y are as defined above] with a halide represented by the formula [5]:

$$Z^2 - R^5 \quad [5]$$

[wherein $R^5$ is as defined above and $Z^2$ represents a halogen atom (such as chlorine, bromine or iodine atom)] or with $CF_2=CF_2$.

Examples of the halide [5] are dibromodifluoromethane, iodotrifluoromethane, bromotrifluoromethane, bromochlorodifluoromethane, chlorodifluoromethane, 1-bromo-2-chlorotetrafluoroethane and 1,2-dibromotetrafluoroethane.

This reaction is carried out usually at a temperature of about −5° C. to 150° C. for about 1–24 hours in a solvent in the presence of a dehydrohalogenating agent.

As the dehydrohalogenating agent used optionally, mention may be made of, for example, organic bases such as pyridine, triethylamine and N,N-diethylaniline, inorganic bases such as sodium hydroxide, potassium hydroxide, sodium carbonate, potassium carbonate, sodium hydrogencarbonate, calcium carbonate and sodium hydride, and alkali metal alkoxides such as sodium methoxide, potassium tert-butoxide and sodium ethoxide.

As for the amounts of the reactants, generally, the halide [5] or $CF_2=CF_2$ is used in an amount of 1–5 mols and the dehydrohalogenating agent used optionally is used in an amount of 1–10 mols or more for 1 mol of the mercaptan [4].

As examples of the solvent, mention may be made of aliphatic hydrocarbon solvents such as hexane, heptane, ligroin and petroleum ether; aromatic hydrocarbon solvents such as benzene; halogenated hydrocarbon solvents such as dichloroethane, chlorobenzene and dichlorobenzene; ether solvents such as diethyl ether, diisopropyl ether, dioxane, tetrahydrofuran and ethylene glycol dimethyl ether; ketone solvents such as acetone, methyl ethyl ketone, methyl isobutyl ketone, isophorone and cyclohexanone; ester solvents such as ethyl acetate and butyl acetate; nitro compound solvents such as nitroethane and nitrobenzene; nitrile solvents such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane; water; and mixtures thereof.

After the completion of the reaction, the desired present compound can be isolated by carrying out usual after-treatments such as extraction with organic solvents and concentration. If necessary, the product can be further purified by chromatography, distillation, recrystallization or the like.

(Process 3)

(Process for the preparation of the present compound represented by the formula [1] where n is 1 or 2):

The present compound where n is 1 or 2 can be prepared by oxidizing the present compound where n is 0.

Examples of the oxidizing agent used are organic peroxides such as hydrogen peroxide and tert-butylhydroperoxide; organic peracids such as m-chloroperbenzoic acid and peracetic acid; metal compounds such as chromic anhydride; peroxosulfuric acid or salts thereof; and sulfur oxides. The amount of the oxidizing agent used is usually an excess amount of 1 mol or more per 1 mol of the present compound where n is 0 in the case of preparing the present compound where n is 1 and an excess amount of 2 mols or more per 1 mol of the present compound where n is 0 in the case of preparing the present compound where n is 2.

This reaction is carried out usually at a temperature of about −5° C. to 150° C. for about 1–24 hours in a solvent.

As examples of the solvent used, mention may be made of aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ester solvents such as ethyl acetate and butyl acetate; nitro compounds such as nitroethane and nitrobenzene; acid amides such as formamide, N,N-dimethylformamide and N,N-dimethylacetamide; sulfur compounds such as sulfolane; organic acids such as acetic acid; water; and mixtures thereof.

After the completion of the reaction, the desired present compound can be isolated, if necessary, by removing excess oxidizing agent with a reducing agent such as aqueous sodium sulfite solution and carrying out usual after-treatments such as extraction with organic solvents and concentration. If necessary, the product can be further purified by chromatography, distillation, recrystallization or the like.

(Process 4)

[Process for the preparation of the present compound represented by the formula [1] where $R^1$ is $NR^{21}R^{31}$ (in which $R^{21}$ and $R^{31}$ are the same or different and each represent an alkyl group, a cycloalkyl group, an alkoxyalkyl group, an alkylthioalkyl group, an alkoxycarbonyl group or an alkanoyl group)]:

The said present compound can be prepared by reacting the present compound where $R^1$ is an amino group with a halide derivative represented by the formula [6] or [7]:

$$R^{21}-Z^2 \qquad [6]$$

and/or

$$R^{31}-Z^2 \qquad [7]$$

[wherein $R^{21}$, $R^{31}$ and $Z^2$ are as defined above] usually in the presence of a dehydrohalogenating agent.

As the dehydrohalogenating agent used, mention may be made of, for example, organic bases such as pyridine, triethylamine and N,N-diethylaniline, inorganic bases such as sodium hydroxide, potassium hydroxide, sodium carbonate, potassium carbonate, sodium hydrogencarbonate, calcium carbonate and sodium hydride, and alkali metal alkoxides such as sodium methoxide and sodium ethoxide.

As for the amounts of the reactants, generally, the halide derivative [6] and/or [7] is used in an amount of 1–2 mols and the dehydrohalogenating agent is used in an amount of 1–4 mols for 1 mol of the present compound where $R^1$ is an amino group.

This reaction is carried out usually at a temperature of about −5° C. to 150° C. for about 1–24 hours in a solvent.

As examples of the solvent used, mention may be made of aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ester solvents such as ethyl acetate and butyl acetate; nitro compounds such as nitroethane and nitrobenzene; nitrile solvents such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane; and mixtures thereof.

After the completion of the reaction, the desired present compound can be isolated by carrying out usual after-treatments such as extraction with organic solvents and concentration. If necessary, the product can be further purified by chromatography, distillation, recrystallization or the like.

(Process 5)

(Process for the preparation of the present compound represented by the formula [1] where $R^1$ is a halogen atom):

The present compound where $R^1$ is a halogen atom can be prepared by reacting the present compound where $R^1$ is an amino group with a nitrite ester represented by the formula [8]:

$$R^7-ONO_2 \qquad [8]$$

[where $R^7$ represents an alkyl group (for example, tert-butyl group or isoamyl group)] in the presence of a haloform (such as chloroform, bromoform or iodoform).

As for the amounts of the reactants, usually, the nitrite ester [8] is used in an amount of 1–4 mols and the haloform is used in an amount of 1–50 mols for 1 mol of the present compound where $R^1$ is an amino group.

This reaction is carried out usually at a reaction temperature of about −5° C. to 150° C. for about 1–24 hours in a solvent.

After the completion of the reaction, the desired present compound can be isolated by carrying out usual after-treatments such as concentration. If necessary, the product can be further purified by chromatography, distillation, recrystallization or the like.

(Process 6)

[Process for the preparation of the present compound represented by the formula [1] where $R^1$ is $NR^{22}R^{32}$ (in which $R^{22}$ and $R^{32}$ each represent $R^2$ other than hydrogen atom and $R^3$ other than hydrogen atom and $R^2$ and $R^3$ are as defined above]:

The desired present compound can be prepared by reacting the present compound where $R^1$ is a halogen atom (such as chlorine, bromine or iodine atom) with an amine derivative represented by the formula [9]:

$$HN(R^{22})R^{32} \qquad [9]$$

[wherein $R^{22}$ and $R^{32}$ are as defined above], if necessary, in the presence of a dehydrohalogenating agent.

As the dehydrohalogenating agent used, mention may be made of, for example, organic bases such as pyridine, triethylamine and N,N-diethylaniline, inorganic bases such as sodium hydroxide, potassium hydroxide, sodium carbonate, potassium carbonate, sodium hydrogencarbonate, calcium carbonate and sodium hydride, and alkali metal alkoxides such as sodium methoxide and sodium ethoxide in addition to the amine derivatives [9] per se.

As for the amounts of the reactants, usually, the amine derivative [9] is used in an amount of 1–2 mols and the dehydrohalogenating agent is used in an amount of 1–4 mols for 1 mol of the present compound where $R^1$ is a halogen atom. When the amine derivative [9] per se is also allowed to act as the dehydrohalogenating agent, the amine derivative can be used in a highly excess amount.

This reaction is carried out usually at a temperature of about −5° C. to 150° C. for about 1–24 hours in a solvent and, if necessary, in a pressure vessel.

The solvent is not necessarily used. If the solvent is used, examples thereof are aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ketone solvents such as acetone, methyl ethyl ketone and methyl isobutyl ketone; ester solvents such as ethyl acetate and butyl acetate; nitro compounds such as nitroethane and nitrobenzene; nitrile solvents such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane; and mixtures thereof.

After the completion of the reaction, the desired present compound can be isolated by carrying out usual after-treatments such as concentration. If necessary, the product can be further purified by chromatography, distillation, recrystallization or the like.

(Process 7)

[Process for the preparation of the present compound represented by the formula [1] where $R^1$ is $N=CR^9(OR^8)$ [in which $R^9$ represents a hydrogen atom or an alkyl group (for example, a $C_1$–$C_4$ alkyl group such as methyl group and ethyl group) and $R^8$ represents an alkyl group (for example, a $C_1$–$C_4$ alkyl group such as methyl group and ethyl group)]:

The desired present compound can be prepared by reacting the present compound where $R^1$ is an amino group with an orthoester derivative represented by the formula [10]:

$$R^9C(OR^8)_3 \qquad [10]$$

[wherein $R^9$ and $R^8$ are as defined above], usually, in the presence of an acid catalyst.

The reaction is carried out usually at a reaction temperature of about −5° C. to 150° C. for about 1–24 hours.

The acid used optionally includes, for example, inorganic acids such as hydrochloric acid and sulfuric acid, organic acids such as acetic acid and p-toluenesulfonic acid, and Lewis acids such as boron trifluoride.

As for the amounts of the reactants, usually, the orthoester derivative [10] is in an amount of 1–7 mols for 1 mol of the present compound where $R^1$ is an amino group.

The solvent is not necessarily used. If the solvent is used, examples thereof are aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ester solvents such as ethyl acetate and butyl acetate; nitro compounds such as nitroethane and nitrobenzene; nitrile solvents such as acetonitrile and isobutyronitrile; acid amides such as formamide, N,N-dimethylformamide and N,N-dimethylacetamide; sulfur compounds such as dimethyl sulfoxide and sulfolane; and mixtures thereof.

After the completion of the reaction, the desired present compound can be isolated' by carrying out usual after-

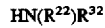

treatments such as concentration. If necessary, the product can be further purified by chromatography, distillation, recrystallization or the like.

(Process 8)

[Process for the preparation of the present compound represented by the formula [1] where $R^1$ is $NHR^{33}$ (in which $R^{33}$ represents an alkyl group]:

The desired present compound can be prepared by reducing the present compound where $R^1$ is $N=CR^9(OR^8)$ (in which $R^9$ and $R^8$ are as defined above) with a metal hydride in the presence or absence of an acid catalyst or hydrogenating the compound in the presence of a hydrogenation catalyst.

The reaction is carried out usually at a temperature of about $-5°$ C. to $150°$ C. for about 1-24 hours and usually in a solvent and, if necessary, in the presence of an acid catalyst when the metal hydride is used.

The acids used include, for example, inorganic acids such as hydrochloric acid and sulfuric acid, organic acids such as acetic acid and p-toluenesulfonic acid, and Lewis acids such as boron trifluoride.

The metal hydrides when the reduction is carried out therewith include, for example, sodium borohydride and lithium borohydride.

The catalysts used for carrying out the hydrogenation include, for example, platinum oxide and Pd/C.

As for the amounts of the reactants, usually, the metal hydride is used in an amount of ½-10 mols for 1 mol of the present compound where $R^1$ is $N=CR^9(OR^8)$.

As examples of the solvent, mention may be made of aliphatic hydrocarbon solvents such as hexane, heptane, ligroin and petroleum ether; aromatic hydrocarbon solvents such as benzene, toluene and xylene; halogenated hydrocarbon solvents such as dichloroethane, chlorobenzene and dichlorobenzene; alcohol solvents such as methanol, ethanol and isopropyl alcohol; ether solvents such as diethyl ether, diisopropyl ether, dioxane, tetrahydrofuran and ethylene glycol dimethyl ether; ester solvents such as ethyl acetate and butyl acetate; and mixtures thereof.

After the completion of the reaction, the desired present compound can be isolated by carrying out usual after-treatments such as extraction with organic solvents and concentration. If necessary, the product can be further purified by chromatography, distillation, recrystallization or the like.

(Process 9)

[Process for the preparation of (i) the present compound represented by the formula [1] where $R^1$ is $NR^2R^3$ in which $R^2$ is a hydrogen atom and $R^3$ is a 2-tetrahydropyranyl group, (ii) the present compound where $R^1$ is a 1-pyrrolyl group, or (iii) the present compound where $R^1$ is a group represented by $N=CR^4R^{61}$ (where $R^4$ is as defined above and $R^{61}$ represents a hydrogen atom, an alkyl group or a dialkylamino group)]:

The desired present compound can be prepared by reacting the present compound where $R^1$ is an amino group with (i) dihydropyran, (ii) 2,6-dimethoxytetrahydrofuran or (iii-1) a carbonyl compound represented by the formula [11]:

$$R^4-C(=O)-R^9 \qquad [11]$$

(wherein $R^4$ and $R^9$ are as defined above) or (iii-2) an acetal represented by the formula [12]:

$$(R^8O)_2C(R^4)R^{61} \qquad [12]$$

(wherein $R^4$, $R^8$ and $R^{61}$ are as defined above).

The reaction is carried out usually at a reaction temperature of about $-5°$ C. to $150°$ C. for about 1-24 hours and usually in a solvent or without solvent, usually, in the presence of an acid in a catalytic amount with removing water from the reaction system by a water separator or the like if water is produced.

The acids used include, for example, inorganic acids such as hydrochloric acid and sulfuric acid, organic acids such as acetic acid and p-toluenesulfonic acid, and Lewis acids such as boron trifluoride.

As for the amounts of the reactants, usually, dihydropyran, 2,6-dimethoxytetrahydrofuran, the carbonyl compound [11] and the acetal [12] are used in an amount of 1-20 mols for 1 mol of the present compound where R1 is an amino group, respectively.

As examples of the solvent, mention may be made of aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ester solvents such as ethyl acetate and butyl acetate; nitro compounds such as nitroethane and nitrobenzene; and mixtures thereof.

After the completion of the reaction, the desired present compound can be isolated by carrying out usual after-treatments such as concentration. If necessary, the product can be further purified by chromatography, distillation, recrystallization or the like.

(Process 10)

[Process for the preparation of the present compound represented by the formula [1] wherein $R^1$ is $NHR^{34}$ (in which $R^{34}$ represents an alkoxyalkyl group or an alkylthioalkyl group)]:

The desired present compound can be prepared by reacting the present compound where $R^1$ is a group represented by $N=CR^4R^9$ (in which $R^4$ and $R^9$ are as defined above) with a compound represented by the formula [13]:

$$R^7AH \qquad [13]$$

[wherein A represents an oxygen atom or a sulfur atom and $R^7$ is as defined above] in the presence of an acid catalyst.

As for the amounts of the reactants, usually, the compound [13] is in an amount of 1-10 mols for 1 mol of the present compound where $R^1$ is $N=CR^4R^9$.

The acids used optionally include, for example, inorganic acids such as hydrochloric acid and sulfuric acid, organic acids such as acetic acid and p-toluenesulfonic acid, and Lewis acids such as boron trifluoride.

The reaction is carried out usually at a reaction temperature of about $-5°$ C.$-150°$ C. for about 1-24 hours in a solvent.

Examples of the solvent used are aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ester solvents such as ethyl acetate and butyl acetate; nitro compounds such as nitroethane and nitrobenzene; sulfur compounds such as dimethyl sulfoxide and sulfolane; and mixtures thereof. When the compound [13] is liquid, the compound [13] per se may be used as the solvent.

After the completion of the reaction, the desired present compound can be isolated by carrying out usual after-treatments such as concentration. If necessary, the product can be further purified by chromatography, distillation, recrystallization or the like.

The disulfide compound [2] and the mercaptan [4] which are intermediates in the preparation of the present compound can be prepared, for example, in accordance with the following scheme.

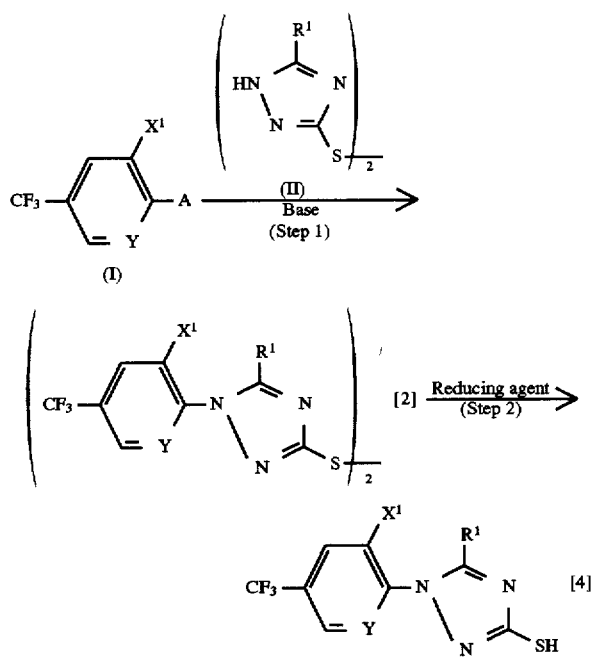

[wherein A represents a halogen atom (fluorine atom, chlorine atom or the like) and $X^1$, Y and $R^1$ are as defined above].

The reaction of the step 1 is carried out usually at a reaction temperature of about −5° C.–150° C. for about 1–24 hours in a solvent in the presence of a base.

As the bases used, mention may be made of, for example, organic bases such as pyridine, triethylamine and N,N-diethylaniline, inorganic bases such as sodium hydroxide, potassium hydroxide, sodium carbonate, potassium carbonate, sodium hydrogencarbonate, calcium carbonate and sodium hydride, and alkali metal alkoxides such as sodium methoxide and sodium ethoxide.

As for the amounts of the reactants, usually, the compound represented by the formula [I] is used in an amount of 2–4 mols and the base is used in an amount of 2–4 mols for 1 mol of the disulfide represented by the formula [II].

Examples of the solvent used are aliphatic hydrocarbon solvents such as hexane, heptane, ligroin and petroleum ether; aromatic hydrocarbon solvents such as benzene, toluene and xylene; halogenated hydrocarbon solvents such as chloroform, carbon tetrachloride, dichloroethane, chlorobenzene and dichlorobenzene; ether solvents such as diethyl ether, diisopropyl ether, dioxane, tetrahydrofuran and ethylene glycol dimethyl ether; ketone solvents such as acetone, methyl ethyl ketone, methyl isobutyl ketone, isophorone and cyclohexanone; ester solvents such as ethyl acetate and butyl acetate; nitro compounds such as nitroethane and nitrobenzene; nitrile solvents such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane; and mixtures thereof.

After the completion of the reaction, the desired disulfide compound [2] can be isolated by carrying out usual after-treatments such as extraction with organic solvents and concentration. If necessary, the product can be further purified by chromatography, distillation, recrystallization or the like.

The compounds represented by the formula [I] can be prepared by the processes described, for example, in U.S. Pat. Nos. 3,888,932 and 3,928,416, European Patent Laid-Open Application Nos.23,100 and 34,402, West German Patent Laid-Open Application Nos.2,606,393 and 3,545, 570, U.S. Pat. No. 4,181,041, J. Org. Chem., 25, 1710 (1960), British Patent Laid-Open Application Nos.2,002,368 and 1,121,211, JP-A-59-20,269 and U.S. Pat. No. 5,109,004 and processes similar to these processes.

The disulfides represented by the formula [II] are prepared, for example, by the process described in JP-A-3-153676 or process similar to this process.

The reaction of the step 2 is carried out usually at a reaction temperature of about −5° C.–150° C. for about 1–24 hours in a solvent.

As the reducing agents used, mention may be made of, for example, metals in the presence of acids such as zinc in the presence of acid and tin in the presence of acid; metal hydrides such as lithium aluminum hydride and sodium borohydride; sodium sulfide, potassium sulfide and triphenylphosphine.

The amount of the reducing agent is usually 1–10 mols for 1 mol of the disulfide compound [2].

Examples of the solvent used are aliphatic hydrocarbon solvents such as hexane, heptane, ligroin and petroleum ether; aromatic hydrocarbon solvents such as benzene, toluene and xylene; ether solvents such as diethyl ether, diisopropyl ether, dioxane, tetrahydrofuran and ethylene glycol dimethyl ether; water; and mixtures thereof.

After the completion of the reaction, the desired mercaptan [3] can be isolated by carrying out usual after-treatments such as extraction with organic solvents and concentration. If necessary, the product can be further purified by chromatography, distillation, recrystallization or the like.

Examples of the present compounds are as shown in the following table. (The compounds are shown by the definitions of the substituents in the formula [1]. In the table, Ph denotes phenyl group, Va denotes 4-hydroxy-3-methoxyphenyl group, and tBu or t-Bu denotes tert-butyl group.)

TABLE 1

| $X^1$ | Y | $R^1$ | $R^5$ | n |
|---|---|---|---|---|
| Cl | CCl | H | $CF_3$ | 0 |
| Cl | CCl | $CH_3$ | $CF_3$ | 0 |
| Cl | CCl | $NH_2$ | $CF_3$ | 0 |
| Cl | CCl | H | $CF_3$ | 1 |
| Cl | CCl | $CH_3$ | $CF_3$ | 1 |
| Cl | CCl | $NH_2$ | $CF_3$ | 1 |
| Cl | CCl | $NH_2$ | $CF_3$ | 2 |
| Cl | CCl | H | $CF_2Br$ | 0 |
| Cl | CCl | $CH_3$ | $CF_2Br$ | 0 |

TABLE 1-continued

| $X^1$ | Y | $R^1$ | $R^5$ | n |
|---|---|---|---|---|
| Cl | CCl | $NH_2$ | $CF_2Br$ | 0 |
| Cl | CCl | H | $CF_2Br$ | 1 |
| Cl | CCl | $CH_3$ | $CF_2Br$ | 1 |
| Cl | CCl | $NH_2$ | $CF_2Br$ | 1 |
| Cl | CCl | $NH_2$ | $CF_2Br$ | 2 |
| Cl | CCl | H | $CF_2H$ | 0 |
| Cl | CCl | $CH_3$ | $CF_2H$ | 0 |
| Cl | CCl | $NH_2$ | $CF_2H$ | 0 |
| Cl | CCl | H | $CF_2H$ | 1 |
| Cl | CCl | $CH_3$ | $CF_2H$ | 1 |
| Cl | CCl | $NH_2$ | $CF_2H$ | 1 |
| Cl | CCl | $NH_2$ | $CF_2H$ | 2 |
| Cl | CCl | H | $CF_2Cl$ | 0 |
| Cl | CCl | $CH_3$ | $CF_2Cl$ | 0 |
| Cl | CCl | $NH_2$ | $CF_2Cl$ | 0 |
| Cl | CCl | H | $CF_2Cl$ | 1 |
| Cl | CCl | $CH_3$ | $CF_2Cl$ | 1 |
| Cl | CCl | $NH_2$ | $CF_2Cl$ | 1 |
| Cl | CCl | $NH_2$ | $CF_2Cl$ | 2 |
| $NO_2$ | CCl | H | $CF_3$ | 0 |
| $NO_2$ | CCl | $CH_3$ | $CF_3$ | 0 |
| $NO_2$ | CCl | $NH_2$ | $CF_3$ | 0 |
| $NO_2$ | CCl | H | $CF_3$ | 1 |
| $NO_2$ | CCl | $CH_3$ | $CF_3$ | 1 |
| $NO_2$ | CCl | $NH_2$ | $CF_3$ | 1 |
| $NO_2$ | CCl | $NH_2$ | $CF_3$ | 2 |
| $NO_2$ | CCl | H | $CF_2Br$ | 0 |
| $NO_2$ | CCl | $CH_3$ | $CF_2Br$ | 0 |
| $NO_2$ | CCl | $NH_2$ | $CF_2Br$ | 0 |
| $NO_2$ | CCl | H | $CF_2Br$ | 1 |
| $NO_2$ | CCl | $CH_3$ | $CF_2Br$ | 1 |
| $NO_2$ | CCl | $NH_2$ | $CF_2Br$ | 1 |
| $NO_2$ | CCl | $NH_2$ | $CF_2Br$ | 2 |
| $NO_2$ | CCl | H | $CF_2H$ | 0 |
| $NO_2$ | CCl | $CH_3$ | $CF_2H$ | 0 |
| $NO_2$ | CCl | $NH_2$ | $CF_2H$ | 0 |
| $NO_2$ | CCl | H | $CF_2H$ | 1 |
| $NO_2$ | CCl | $CH_3$ | $CF_2H$ | 1 |
| $NO_2$ | CCl | $NH_2$ | $CF_2H$ | 1 |
| $NO_2$ | CCl | $NH_2$ | $CF_2H$ | 2 |
| $NO_2$ | CCl | H | $CF_2Cl$ | 0 |
| $NO_2$ | CCl | $CH_3$ | $CF_2Cl$ | 0 |
| $NO_2$ | CCl | $NH_2$ | $CF_2Cl$ | 0 |
| $NO_2$ | CCl | H | $CF_2Cl$ | 1 |
| $NO_2$ | CCl | $CH_3$ | $CF_2Cl$ | 1 |
| $NO_2$ | CCl | $NH_2$ | $CF_2Cl$ | 1 |
| $NO_2$ | CCl | $NH_2$ | $CF_2Cl$ | 2 |
| CN | CCl | H | $CF_3$ | 0 |
| CN | CCl | $CH_3$ | $CF_3$ | 0 |
| CN | CCl | $CH_3$ | $CF_2Cl$ | 1 |
| CN | CCl | H | $CF_3$ | 1 |
| CN | CCl | $CH_3$ | $CF_3$ | 1 |
| CN | CCl | H | $CF_2Br$ | 0 |
| CN | CCl | $CH_3$ | $CF_2Br$ | 0 |
| CN | CCl | H | $CF_2Br$ | 1 |
| CN | CCl | $CH_3$ | $CF_2Br$ | 1 |
| CN | CCl | H | $CF_2H$ | 0 |
| CN | CCl | $CH_3$ | $CF_2H$ | 0 |
| CN | CCl | H | $CF_2H$ | 1 |
| CN | CCl | $CH_3$ | $CF_2H$ | 1 |
| CN | CCl | H | $CF_2Cl$ | 0 |
| CN | CCl | $CH_3$ | $CF_2Cl$ | 0 |
| CN | CCl | H | $CF_2Cl$ | 1 |
| Cl | N | H | $CF_3$ | 0 |
| Cl | N | $CH_3$ | $CF_3$ | 0 |
| Cl | N | $NH_2$ | $CF_3$ | 0 |
| Cl | N | H | $CF_3$ | 1 |
| Cl | N | $CH_3$ | $CF_3$ | 1 |
| Cl | N | $NH_2$ | $CF_3$ | 1 |
| Cl | N | $NH_2$ | $CF_3$ | 2 |
| Cl | N | H | $CF_2Br$ | 0 |
| Cl | N | $CH_3$ | $CF_2Br$ | 0 |
| Cl | N | $NH_2$ | $CF_2Br$ | 0 |
| Cl | N | H | $CF_2Br$ | 1 |
| Cl | N | $CH_3$ | $CF_2Br$ | 1 |
| Cl | N | $NH_2$ | $CF_2Br$ | 1 |
| Cl | N | $NH_2$ | $CF_2Br$ | 2 |
| Cl | N | H | $CF_2H$ | 0 |
| Cl | N | $CH_3$ | $CF_2H$ | 0 |
| Cl | N | $NH_2$ | $CF_2H$ | 0 |
| Cl | N | H | $CF_2H$ | 1 |
| Cl | N | $CH_3$ | $CF_2H$ | 1 |
| Cl | N | $NH_2$ | $CF_2H$ | 1 |
| Cl | N | $NH_2$ | $CF_2H$ | 2 |
| Cl | N | H | $CF_2Cl$ | 0 |
| Cl | N | $CH_3$ | $CF_2Cl$ | 0 |
| Cl | N | $NH_2$ | $CF_2Cl$ | 0 |
| Cl | N | H | $CF_2Cl$ | 1 |
| Cl | N | $CH_3$ | $CF_2Cl$ | 1 |
| Cl | N | $NH_2$ | $CF_2Cl$ | 1 |
| Cl | N | $NH_2$ | $CF_2Cl$ | 2 |
| Cl | CCl | N=CHPh | $CF_3$ | 0 |
| Cl | CCl | N=CHPh | $CF_3$ | 1 |
| Cl | CCl | N=CHPh | $CF_3$ | 2 |
| Cl | CCl | N=CHPh | $CF_2Br$ | 0 |
| Cl | CCl | N=CHPh | $CF_2Br$ | 1 |
| Cl | CCl | N=CHPh | $CF_2Br$ | 2 |
| Cl | CCl | N=CHPh | $CF_2H$ | 0 |
| Cl | CCl | N=CHPh | $CF_2H$ | 1 |
| Cl | CCl | N=CHPh | $CF_2H$ | 2 |
| Cl | CCl | N=CHPh | $CF_2Cl$ | 0 |
| Cl | CCl | N=CHPh | $CF_2Cl$ | 1 |
| Cl | CCl | N=CHPh | $CF_2Cl$ | 2 |
| Cl | CCl | N=CHVa | $CF_3$ | 0 |
| Cl | CCl | N=CHVa | $CF_3$ | 1 |
| Cl | CCl | N=CHVa | $CF_3$ | 2 |
| Cl | CCl | N=CHVa | $CF_2Br$ | 0 |
| Cl | CCl | N=CHVa | $CF_2Br$ | 1 |
| Cl | CCl | N=CHVa | $CF_2Br$ | 2 |
| Cl | CCl | N=CHVa | $CF_2H$ | 0 |
| Cl | CCl | N=CHVa | $CF_2H$ | 1 |
| Cl | CCl | N=CHVa | $CF_2H$ | 2 |
| Cl | CCl | N=CHVa | $CF_2Cl$ | 0 |
| Cl | CCl | N=CHVa | $CF_2Cl$ | 1 |
| Cl | CCl | N=CHVa | $CF_2Cl$ | 2 |
| Cl | CCl | $NHC_2H_5$ | $CF_3$ | 0 |
| Cl | CCl | $NHC_2H_5$ | $CF_3$ | 1 |
| Cl | CCl | $NHC_2H_5$ | $CF_3$ | 2 |
| Cl | CCl | $NHC_2H_5$ | $CF_2Br$ | 0 |
| Cl | CCl | $NHC_2H_5$ | $CF_2Br$ | 1 |
| Cl | CCl | $NHC_2H_5$ | $CF_2Br$ | 2 |
| Cl | CCl | $NHC_2H_5$ | $CF_2H$ | 0 |
| Cl | CCl | $NHC_2H_5$ | $CF_2H$ | 1 |
| Cl | CCl | $NHC_2H_5$ | $CF_2H$ | 2 |
| Cl | CCl | $NHC_2H_5$ | $CF_2Cl$ | 0 |
| Cl | CCl | $NHC_2H_5$ | $CF_2Cl$ | 1 |
| Cl | CCl | $NHC_2H_5$ | $CF_2Cl$ | 2 |
| Cl | CCl | $N(C_2H_5)_2$ | $CF_3$ | 0 |
| Cl | CCl | $N(C_2H_5)_2$ | $CF_3$ | 1 |
| Cl | CCl | $N(C_2H_5)_2$ | $CF_3$ | 2 |
| Cl | CCl | $N(C_2H_5)_2$ | $CF_2Br$ | 0 |
| Cl | CCl | $N(C_2H_5)_2$ | $CF_2Br$ | 1 |
| Cl | CCl | $N(C_2H_5)_2$ | $CF_2Br$ | 2 |
| Cl | CCl | $N(C_2H_5)_2$ | $CF_2H$ | 0 |
| Cl | CCl | $N(C_2H_5)_2$ | $CF_2H$ | 1 |
| Cl | CCl | $N(C_2H_5)_2$ | $CF_2H$ | 2 |
| Cl | CCl | $N(C_2H_5)_2$ | $CF_2Cl$ | 0 |
| Cl | CCl | $N(C_2H_5)_2$ | $CF_2Cl$ | 1 |
| Cl | CCl | $N(C_2H_5)_2$ | $CF_2Cl$ | 2 |
| $NO_2$ | CCl | N=CHPh | $CF_3$ | 0 |
| $NO_2$ | CCl | N=CHPh | $CF_3$ | 1 |
| $NO_2$ | CCl | N=CHPh | $CF_3$ | 2 |
| $NO_2$ | CCl | N=CHPh | $CF_2Br$ | 0 |
| $NO_2$ | CCl | N=CHPh | $CF_2Br$ | 1 |
| $NO_2$ | CCl | N=CHPh | $CF_2Br$ | 2 |
| $NO_2$ | CCl | N=CHPh | $CF_2H$ | 0 |
| $NO_2$ | CCl | N=CHPh | $CF_2H$ | 1 |
| $NO_2$ | CCl | N=CHPh | $CF_2H$ | 2 |
| $NO_2$ | CCl | N=CHPh | $CF_2Cl$ | 0 |
| $NO_2$ | CCl | N=CHPh | $CF_2Cl$ | 1 |
| $NO_2$ | CCl | N=CHPh | $CF_2Cl$ | 2 |
| $NO_2$ | CCl | N=CHVa | $CF_3$ | 0 |
| $NO_2$ | CCl | N=CHVa | $CF_3$ | 1 |
| $NO_2$ | CCl | N=CHVa | $CF_3$ | 2 |

TABLE 1-continued

| X¹ | Y | R¹ | R⁵ | n |
|---|---|---|---|---|
| NO₂ | CCl | N=CHVa | CF₂Br | 0 |
| NO₂ | CCl | N=CHVa | CF₂Br | 1 |
| NO₂ | CCl | N=CHVa | CF₂Br | 2 |
| NO₂ | CCl | N=CHVa | CF₂H | 0 |
| NO₂ | CCl | N=CHVa | CF₂H | 1 |
| NO₂ | CCl | N=CHVa | CF₂H | 2 |
| NO₂ | CCl | N=CHVa | CF₂Cl | 0 |
| NO₂ | CCl | N=CHVa | CF₂Cl | 1 |
| NO₂ | CCl | N=CHVa | CF₂Cl | 2 |
| NO₂ | CCl | NHC₂H₅ | CF₃ | 0 |
| NO₂ | CCl | NHC₂H₅ | CF₃ | 1 |
| NO₂ | CCl | NHC₂H₅ | CF₃ | 2 |
| NO₂ | CCl | NHC₂H₅ | CF₂Br | 0 |
| NO₂ | CCl | NHC₂H₅ | CF₂Br | 1 |
| NO₂ | CCl | NHC₂H₅ | CF₂Br | 2 |
| NO₂ | CCl | NHC₂H₅ | CF₂H | 0 |
| NO₂ | CCl | NHC₂H₅ | CF₂H | 1 |
| NO₂ | CCl | NHC₂H₅ | CF₂H | 2 |
| NO₂ | CCl | NHC₂H₅ | CF₂Cl | 0 |
| NO₂ | CCl | NHC₂H₅ | CF₂Cl | 1 |
| NO₂ | CCl | NHC₂H₅ | CF₂Cl | 2 |
| NO₂ | CCl | N(C₂H₅)₂ | CF₃ | 0 |
| NO₂ | CCl | N(C₂H₅)₂ | CF₃ | 1 |
| NO₂ | CCl | N(C₂H₅)₂ | CF₃ | 2 |
| NO₂ | CCl | N(C₂H₅)₂ | CF₂Br | 0 |
| NO₂ | CCl | N(C₂H₅)₂ | CF₂Br | 1 |
| NO₂ | CCl | N(C₂H₅)₂ | CF₂Br | 2 |
| NO₂ | CCl | N(C₂H₅)₂ | CF₂H | 0 |
| NO₂ | CCl | N(C₂H₅)₂ | CF₂H | 1 |
| NO₂ | CCl | N(C₂H₅)₂ | CF₂H | 2 |
| NO₂ | CCl | N(C₂H₅)₂ | CF₂Cl | 0 |
| NO₂ | CCl | N(C₂H₅)₂ | CF₂Cl | 1 |
| NO₂ | CCl | N(C₂H₅)₂ | CF₂Cl | 2 |
| Cl | N | N=CHPh | CF₃ | 0 |
| Cl | N | N=CHPh | CF₃ | 1 |
| Cl | N | N=CHPh | CF₃ | 2 |
| Cl | N | N=CHPh | CF₂Br | 0 |
| Cl | N | N=CHPh | CF₂Br | 1 |
| Cl | N | N=CHPh | CF₂Br | 2 |
| Cl | N | N=CHPh | CF₂H | 0 |
| Cl | N | N=CHPh | CF₂H | 1 |
| Cl | N | N=CHPh | CF₂H | 2 |
| Cl | N | N=CHPh | CF₂Cl | 0 |
| Cl | N | N=CHPh | CF₂Cl | 1 |
| Cl | N | N=CHPh | CF₂Cl | 2 |
| Cl | N | N=CHVa | CF₃ | 0 |
| Cl | N | N=CHVa | CF₃ | 1 |
| Cl | N | N=CHVa | CF₃ | 2 |
| Cl | N | N=CHVa | CF₂Br | 0 |
| Cl | N | N=CHVa | CF₂Br | 1 |
| Cl | N | N=CHVa | CF₂Br | 2 |
| Cl | N | N=CHVa | CF₂H | 0 |
| Cl | N | N=CHVa | CF₂Cl | 1 |
| Cl | N | N=CHVa | CF₂Cl | 2 |
| Cl | N | N=CHVa | CF₂H | 1 |
| Cl | N | N=CHVa | CF₂H | 2 |
| Cl | N | N=CHVa | CF₂Cl | 0 |
| Cl | N | N=CHVa | CF₂Cl | 1 |
| Cl | N | N=CHVa | CF₂Cl | 2 |
| Cl | N | NHC₂H₅ | CF₃ | 0 |
| Cl | N | NHC₂H₅ | CF₃ | 1 |
| Cl | N | NHC₂H₅ | CF₃ | 2 |
| Cl | N | NHC₂H₅ | CF₂Br | 0 |
| Cl | N | NHC₂H₅ | CF₂Br | 1 |
| Cl | N | NHC₂H₅ | CF₂Br | 2 |
| Cl | N | NHC₂H₅ | CF₂H | 0 |
| Cl | N | NHC₂H₅ | CF₂H | 1 |
| Cl | N | NHC₂H₅ | CF₂H | 2 |
| Cl | N | NHC₂H₅ | CF₂Cl | 0 |
| Cl | N | NHC₂H₅ | CF₂Cl | 1 |
| Cl | N | NHC₂H₅ | CF₂Cl | 2 |
| Cl | N | N(C₂H₅)₂ | CF₃ | 0 |
| Cl | N | N(C₂H₅)₂ | CF₃ | 1 |
| Cl | N | N(C₂H₅)₂ | CF₃ | 2 |
| Cl | N | N(C₂H₅)₂ | CF₂Br | 0 |
| Cl | N | N(C₂H₅)₂ | CF₂Br | 1 |
| Cl | N | N(C₂H₅)₂ | CF₂Br | 2 |
| Cl | N | N(C₂H₅)₂ | CF₂H | 0 |
| Cl | N | N(C₂H₅)₂ | CF₂H | 1 |
| Cl | N | N(C₂H₅)₂ | CF₂H | 2 |
| Cl | N | N(C₂H₅)₂ | CF₂Cl | 0 |
| Cl | CCl | NHCH₃ | CF₃ | 0 |
| Cl | CCl | NH(CH₂)₂CH₃ | CF₃ | 0 |
| Cl | CCl | NH(CH₂)₃CH₃ | CF₃ | 0 |
| Cl | CCl | NHCH(CH₃)₂ | CF₃ | 0 |
| Cl | CCl | NHCH(CH₃)CH₂CH₃ | CF₃ | 0 |
| Cl | CCl | NHCH₂CH(CH₃)₂ | CF₃ | 0 |
| Cl | CCl | NHC(CH₃)₃ | CF₃ | 0 |
| Cl | CCl | NHCH₂C(CH₃)₃ | CF₃ | 0 |
| Cl | CCl | N(CH₃)CH₂CH₃ | CF₂ | 0 |
| Cl | CCl | N(CH₂)₂ | CF₃ | 0 |
| Cl | CCl | NH-cyclopropyl | CF₃ | 0 |
| Cl | CCl | NH-cyclobutyl | CF₃ | 0 |
| Cl | CCl | NH-cyclopentyl | CF₃ | 0 |
| Cl | CCl | NH-cyclohexyl | CF₃ | 0 |
| Cl | CCl | N-azetidinyl (3-membered) | CF₃ | 0 |
| Cl | CCl | N-azetidinyl (4-membered) | CF₃ | 0 |
| Cl | CCl | N-pyrrolidinyl | CF₃ | 0 |
| Cl | CCl | N-morpholinyl | CF₃ | 0 |
| Cl | CCl | NH-tetrahydropyranyl | CF₃ | 0 |
| Cl | CCl | N-pyrrolyl | CF₃ | 0 |
| Cl | CCl | NH(CH₂)₂OCH₃ | CF₃ | 0 |
| Cl | CCl | NHCH(OCH₃)C(CH₃)₃ | CF₃ | 0 |
| Cl | CCl | NHCH(OCH₂CH₃)C(CH₃)₃ | CF₃ | 0 |
| Cl | CCl | NHCH₂OCH₃ | CF₃ | 0 |
| Cl | CCl | NHCH₂OCH₂CH₃ | CF₃ | 0 |
| Cl | CCl | NHCH₂OCH(CH₃)₂ | CF₃ | 0 |
| Cl | CCl | NHCH₂OCH₂CH₂CH₃ | CF₃ | 0 |
| Cl | CCl | NHCH₂O(CH₂)₃CH₃ | CF₃ | 0 |
| Cl | CCl | NHCH₂OCH(CH₃)CH₂CH₃ | CF₃ | 0 |

TABLE 1-continued

| $X^1$ | Y | $R^1$ | $R^5$ | n |
|---|---|---|---|---|
| Cl | CCl | NHCH$_2$OCH$_2$CH(CH$_3$)$_2$ | CF$_3$ | 0 |
| Cl | CCl | NHCOCH$_3$ | CF$_3$ | 0 |
| Cl | CCl | NHCOCH$_2$CH$_3$ | CF$_3$ | 0 |
| Cl | CCl | NHCO(CH$_2$)$_2$CH$_3$ | CF$_3$ | 0 |
| Cl | CCl | NHCO(CH$_2$)$_3$CH$_3$ | CF$_3$ | 0 |
| Cl | CCl | NHCOCH(CH$_3$)$_2$ | CF$_3$ | 0 |
| Cl | CCl | NHCOCH$_2$CH(CH$_3$)$_3$ | CF$_3$ | 0 |
| Cl | CCl | NH(COCH$_3$)$_2$ | CF$_3$ | 0 |
| Cl | CCl | NH(COCH$_2$CH$_3$)$_2$ | CF$_3$ | 0 |
| Cl | CCl | NH(COCH$_2$CH$_2$)$_2$ | CF$_3$ | 0 |
| Cl | CCl | NH(COCH$_2$CH$_2$CH$_3$)$_2$ | CF$_3$ | 0 |
| Cl | CCl | NHCH(OCH$_3$)C(CH$_3$)$_3$ | CF$_3$ | 1 |
| Cl | CCl | NHCH(OCH$_3$)C(CH$_3$)$_3$ | CF$_3$ | 2 |
| Cl | CCl | NH(CH$_2$)$_2$CH$_3$ | CF$_3$ | 1 |
| Cl | CCl | NH(CH$_2$)$_2$CH$_3$ | CF$_3$ | 2 |
| Cl | CCl | NHCH(OCH$_3$)C(CH$_3$)$_3$ | CF$_2$CH$_3$ | 0 |
| Cl | CCl | NHCH(OCH$_3$)C(CH$_3$)$_3$ | CF$_2$CH$_3$ | 1 |
| Cl | CCl | NHCH(OCH$_3$)C(CH$_3$)$_3$ | CF$_2$CH$_3$ | 2 |
| Cl | CCl | NHCH(OCH$_3$)C(CH$_3$)$_3$ | CF$_2$Br | 0 |
| Cl | CCl | NHCH(OCH$_3$)C(CH$_3$)$_3$ | CF$_2$Br | 1 |
| Cl | CCl | NHCH(OCH$_3$)C(CH$_3$)$_3$ | CF$_2$Br | 2 |
| Cl | CCl | NHCH(OCH$_3$)C(CH$_3$)$_3$ | CF$_2$CF$_2$H | 0 |
| Cl | CCl | NHCH(OCH$_3$)C(CH$_3$)$_2$ | CF$_2$CF$_2$H | 1 |
| Cl | CCl | NHCH(OCH$_3$)C(CH$_3$)$_3$ | CF$_2$CF$_2$H | 2 |
| Cl | CCl | NHCH(OCH$_3$)C(CH$_3$)$_3$ | CF$_2$CF$_2$Br | 0 |
| Cl | CCl | NHCH(OCH$_3$)C(CH$_3$)$_3$ | CF$_2$CF$_2$Br | 1 |
| Cl | CCl | NHCH(OCH$_3$)C(CH$_2$)$_2$ | CF$_2$CF$_2$Br | 2 |
| Cl | CCl | NHCH(OCH$_3$)C(CH$_3$)$_3$ | CF$_2$H | 0 |
| Cl | CCl | NHCH(OCH$_3$)C(CH$_3$)$_3$ | CF$_2$H | 1 |
| Cl | CCl | NHCH(OCH$_3$)C(CH$_3$)$_3$ | CF$_2$H | 2 |
| Cl | CCl | NHCH(OCH$_3$)C(CH$_3$)$_3$ | CH$_2$CF$_3$ | 0 |
| Cl | CCl | NHCH(OCH$_3$)C(CH$_2$)$_3$ | CH$_2$CF$_3$ | 1 |
| Cl | CCl | NHCH(OCH$_3$)C(CH$_3$)$_3$ | CH$_2$CF$_3$ | 2 |
| F | CCl | NHCH(OCH$_3$)C(CH$_3$)$_3$ | CF$_3$ | 0 |
| F | CCl | NHCH(OCH$_3$)C(CH$_3$)$_3$ | CF$_3$ | 1 |
| F | CCl | NHCH(OCH$_3$)C(CH$_3$)$_3$ | CF$_3$ | 2 |
| Cl | CCl | HNC(CH$_3$)$_3$ | CF$_2$CH$_3$ | 0 |
| Cl | CCl | HNC(CH$_3$)$_3$ | CF$_2$CH$_3$ | 1 |
| Cl | CCl | HNC(CH$_3$)$_3$ | CF$_2$CH$_3$ | 2 |
| Cl | CCl | HNC(CH$_3$)$_3$ | CF$_2$Br | 0 |
| Cl | CCl | HNC(CH$_3$)$_3$ | CF$_2$Br | 1 |
| Cl | CCl | HNC(CH$_3$)$_3$ | CF$_2$Br | 2 |
| Cl | CCl | HNC(CH$_3$)$_3$ | CF$_2$CF$_2$H | 0 |
| Cl | CCl | HNC(CH$_3$)$_3$ | CF$_2$CF$_2$H | 1 |
| Cl | CCl | HNC(CH$_3$)$_3$ | CF$_2$CF$_2$H | 2 |
| Cl | CCl | HNC(CH$_3$)$_3$ | CF$_2$CF$_2$Br | 0 |
| Cl | CCl | HNC(CH$_3$)$_3$ | CF$_2$CF$_2$Br | 1 |
| Cl | CCl | HNC(CH$_3$)$_3$ | CF$_2$CF$_2$Br | 2 |
| Cl | CCl | HNC(CH$_3$)$_3$ | CF$_2$H | 0 |
| Cl | CCl | HNC(CH$_3$)$_3$ | CF$_2$H | 1 |
| Cl | CCl | HNC(CH$_3$)$_3$ | CF$_2$H | 2 |
| Cl | CCl | HNC(CH$_3$)$_3$ | CH$_2$CF$_3$ | 0 |
| Cl | CCl | HNC(CH$_3$)$_3$ | CH$_2$CF$_3$ | 1 |
| Cl | CCl | HNC(CH$_3$)$_3$ | CH$_2$CF$_3$ | 2 |
| F | CCl | HNC(CH$_3$)$_3$ | CF$_3$ | 0 |
| F | CCl | HNC(CH$_3$)$_3$ | CF$_3$ | 1 |
| F | CCl | HNC(CH$_3$)$_3$ | CF$_3$ | 2 |
| Cl | CCl | Br | CF$_3$ | 0 |
| Cl | CCl | Br | CF$_3$ | 1 |
| Cl | CCl | Br | CF$_3$ | 2 |
| Cl | CCl | Cl | CF$_3$ | 0 |
| Cl | CCl | Cl | CF$_3$ | 1 |
| Cl | CCl | Cl | CF$_3$ | 2 |
| Cl | CCl | NHCCH$_3$(OCH$_3$)$^t$Bu | CF$_3$ | 0 |
| Cl | CCl | NHCCH$_3$(OCH$_3$)$^t$Bu | CF$_3$ | 1 |
| Cl | CCl | NHCCH$_3$(OCH$_3$)$^t$Bu | CF$_3$ | 2 |
| Cl | CCl | NHCCH$_3$(OCH$_2$CH$_3$)$^t$Bu | CF$_3$ | 0 |
| Cl | CCl | NHCCH$_3$(OCH$_2$CH$_3$)$^t$Bu | CF$_3$ | 1 |
| Cl | CCl | NHCCH$_3$(OCH$_2$CH$_3$)$^t$Bu | CF$_3$ | 2 |
| Cl | CCl | NHCH(OCH$_2$CH$_3$)C(CH$_3$)$_3$ | CF$_3$ | 1 |
| Cl | CCl | NHCH(OCH$_2$CH$_3$)C(CH$_3$)$_3$ | CF$_3$ | 2 |
| Cl | CCl | NHCH(OCH$_2$CH$_3$)C(CH$_3$)$_3$ | CF$_2$Br | 0 |
| Cl | CCl | NHCH(OCH$_2$CH$_3$)C(CH$_3$)$_3$ | CF$_2$Br | 1 |
| Cl | CCl | NHCH(OCH$_2$CH$_3$)C(CH$_3$)$_3$ | CF$_2$Br | 2 |
| Cl | CCl | NHCH(OCH$_2$CH$_3$)C(CH$_3$)$_2$ | CF$_2$CF$_2$H | 0 |
| Cl | CCl | NHCH(OCH$_2$CH$_3$)C(CH$_3$)$_2$ | CF$_2$CF$_2$H | 1 |
| Cl | CCl | NHCH(OCH$_2$CH$_3$)C(CH$_3$)$_3$ | CF$_2$CF$_2$H | 2 |
| Cl | CCl | NHCH(OCH$_2$CH$_3$)C(CH$_3$)$_3$ | CF$_2$H | 0 |
| Cl | CCl | NHCH(OCH$_2$CH$_3$)C(CH$_3$)$_3$ | CF$_2$H | 1 |
| Cl | CCl | NHCH(OCH$_2$CH$_3$)C(CH$_3$)$_3$ | CF$_2$H | 2 |
| Cl | CCl | NHCCH$_3$(OCH$_2$CH$_3$)$^t$Bu | CF$_2$Br | 0 |
| Cl | CCl | NHCCH$_3$(OCH$_2$CH$_3$)$^t$Bu | CF$_2$Br | 1 |
| Cl | CCl | NHCCH$_3$(OCH$_2$CH$_3$)$^t$Bu | CF$_2$Br | 2 |
| Cl | CCl | NHCCH$_3$(OCH$_2$CH$_3$)$^t$Bu | CF$_2$H | 0 |
| Cl | CCl | NHCCH$_3$(OCH$_2$CH$_3$)$^t$Bu | CF$_2$H | 1 |
| Cl | CCl | NHCCH$_3$(OCH$_2$CH$_3$)$^t$Bu | CF$_2$H | 2 |
| Cl | CCl | N=C(OCH$_2$CH$_3$)CH$_3$ | CF$_3$ | 0 |
| Cl | CCl | N=C(OCH$_2$CH$_3$)CH$_2$CH$_3$ | CF$_3$ | 0 |
| Cl | CCl | N=C(CH$_3$)N(CH$_3$)$_2$ | CF$_3$ | 0 |
| Cl | CCl | N=CHC(CH$_3$)$_3$ | CF$_3$ | 0 |
| Cl | CCl | N=CCH$_3$C(CH$_2$)$_3$ | CF$_3$ | 0 |
| Cl | CCl | –N(isothiazolidin-3-one) | CF$_3$ | 0 |
| Cl | CCl | –N(2-t-Bu-1,3-oxazinane) | CF$_3$ | 0 |
| Cl | CCl | –N(2-t-Bu-1,3-thiazinane) | CF$_3$ | 0 |
| Cl | CCl | –N(5,5-dimethyl-isothiazolidin-3-one) | CF$_3$ | 0 |
| Cl | CCl | N=C(OCH$_2$CH$_3$)CH$_2$CH$_2$CH$_3$ | CF$_3$ | 0 |
| Cl | CCl | –N(4-oxopiperidin-1-yl) | CF$_3$ | 0 |
| Cl | CCl | –N(thiomorpholin-4-yl) | CF$_3$ | 0 |
| Cl | CCl | –N(2-oxopyrrolidin-1-yl) | CF$_3$ | 0 |
| Cl | CCl | –N(2,5-dioxopyrrolidin-1-yl) | CF$_3$ | 0 |
| Cl | CCl | –N(3-hydroxy-2,5-dioxopyrrolidin-1-yl) | CF$_3$ | 0 |

TABLE 1-continued

| X¹ | Y | R¹ | R⁵ | n |
|---|---|---|---|---|
| Cl | CCl | 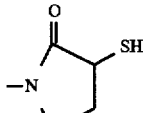 (N-succinimidyl with SH) | $CF_3$ | 0 |
| Cl | CCl | 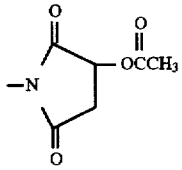 (N-succinimidyl with OC(O)CH₃) | $CF_3$ | 0 |
| Cl | CCl | $NHCH(SCH_2CH_3)C(CH_3)_3$ | $CF_3$ | 0 |
| Cl | CCl | $N(CO_2CH_2CH_3)_2$ | $CF_3$ | 0 |
| Cl | CCl | $NH_2$ | $CF_2CF_2H$ | 0 |
| Cl | CCl | 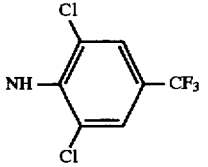 (NH-2,6-dichloro-4-CF₃-phenyl) | $CF_3$ | 0 |
| Cl | CCl | $N(CO_2CH_2CH_2CH_2CH_3)_2$ | $CF_3$ | 0 |
| Cl | CCl | 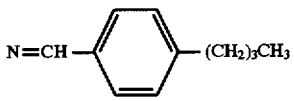 (N=CH-C₆H₄-(CH₂)₃CH₃) | $CF_3$ | 0 |
| Cl | CCl | $NHCOCH_2OCH_3$ | $CF_3$ | 0 |
| Cl | CCl | $NHS(CH_2)_3CH_3$ | $CF_3$ | 0 |
| Cl | CCl | $N(CO_2CH_2CH_2CH_3)_2$ | $CF_3$ | 0 |
| Cl | CCl | $N[CO_2CH(CH_3)_2]_2$ | $CF_3$ | 0 |
| Cl | CCl | $NHCO_2CH(CH_3)_2$ | $CF_3$ | 0 |
| Cl | CCl | $NHCOCH_2$-t-Bu | $CF_3$ | 0 |
| Cl | CCl | $NHSCH(CH_3)_2$ | $CF_3$ | 0 |
| Cl | CCl | $NHSN[CH(CH_3)_2]CH_2CH_2CO_2CH_2CH_3$ | $CF_3$ | 0 |
| Cl | CCl | $N(SO_2CH_3)_2$ | $CF_3$ | 0 |
| Cl | CCl | 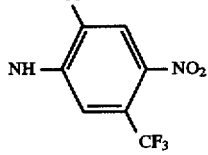 (NH-2-Cl-4-NO₂-5-CF₃-phenyl) | $CF_3$ | 0 |
| Cl | CCl | 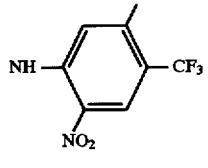 (NH-2-Cl-4-CF₃-5-NO₂-phenyl) | $CF_3$ | 0 |
| Cl | CCl | $NHCH_2SCH_3$ | $CF_3$ | 0 |
| Cl | CCl |  (N-thiomorpholine-like ring) | $CF_3$ | 0 |
| Cl | CCl | $NHSN(CH_3)CO_2(CH_2)_3CH_3$ | $CF_3$ | 0 |
| Cl | CCl | $NHSN(CH_2CH_2CH_2CH_3)_2$ | $CF_3$ | 0 |
| Cl | CCl | 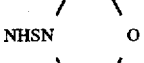 (NHSN-morpholine) | $CF_3$ | 0 |
| Cl | CCl | 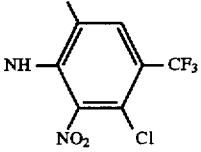 (NH-2-Cl-3-NO₂-4-CF₃-5-NO₂-phenyl) | $CF_3$ | 0 |
| Cl | CCl | $NHSCO_2CH_3$ | $CF_3$ | 0 |
| Cl | CCl | $N(COSCH_2CH_3)_2$ | $CF_3$ | 0 |

The present compounds can be used as agricultural insecticides and acaricides and epidemic preventing insecticides and acaricides.

Examples of insect and other pests (noxious insects and mites) on which the present compounds exhibit controlling effects are as follows:

Insects of Hemiptera order:

Planthoppers such as small brown planthopper, brown rice planthopper and whitebacked rice planthopper, leafhoppers such as green rice leafhopper, aphids, stink bugs, whiteflies, Coccidae, lace bugs, jumping plantlices, etc.

Insects of Lepidoptera order:

Pyralid moths such as rice stem borer, rice leafroller and armyworms such as common cutworm, rice armyworm and cabbage armyworm, sulfur butterflies such as common cabbage worm, leafroller months such as summer fruit tortrix, Carposinidae, lyonetiid moths, oriental tussock moths, , insects of Agrotis spp. such as turnip moth and dark sword grass moth, insects of Heliothis spp, diamondback moth, casemaking clothes moth, webbing clothes moth, etc.

Insects of Diptera order:

Culices such as *Culex pipiens pallens* and *Culex tritaniorhynchus*, striped mosquitoes such as tropical striped mosquito and one-striped mosquito, Anopheles mosquitoes such as chinese anopheles mosquito, midges, house flies such as allies and large houseflies, black flies, flesh flies, anthomyiid flies such as seedcorn maggot, small house fly and onion maggot, fruit flies, vinegar flies, moth flies, horseflies, gnats, biting flies, etc.

Insects of Coleoptera order:

Corn root worms such as western corn root worm and southern corn root worm, scarabs such as cupreous chafer and soybeen beetle, weevils such as maize weevil, ricewater weevil and adzuki been weevil, darkling beetles such as yellow mealworm and red flour beetle, leaf beetles such as striped flea beetle and cucurbit leaf beetle, deathwatch and drugstore beetles, insects of Epilachna spp. such as twenty-eight-spotted ladybird, powder post beetles, false powder-spot beetles, longicorn beetles, Paederus idae Lewis, etc.

Insects of Dictyoptera order:

Cockroaches such as German cockroach, oriental cockroach (*Blatta orientalis*), American cockroach, brown cockroach, Insects of Thysanoptera order:

, flower thrips, etc.

Insects of Hymenoptera order:

Ants, hornets, bethylid wasps, sawflies such as cabbage sawfly, etc.

Insects of Orthoptera order:
Mole crickets, grasshoppers, etc.
Insects of Aphaniptera order:
Human flea, etc.
Insects of Anoplura order:
Lice, phthiridae, etc.
Insects of Isoptera order:
Reticulitermes speratus Kolbe, Formosan subterranean termite, etc.

House dust mites:
Dermatophagoides spp. such as *Dermatophagoides farinae* and *Dermatophagoides pteronyssinus;* Acaridae such as *Tyrophagus putrescentiae* and *Aleuroglyphus ovatus;* Glycyphagus spp. such as *Glycyphagus privatus, Glycyphagus domesticus* and *Glycyphagus destructor;* Cheyetidae such as *Cheyletus malaccensis* and *Cheyletus fortis;* Tarsonemidae; Haplochthoninus simplex; etc.

Spider mites:
Carmine spider mite, two-spotted spider mite, Kanzawa spider mite, citrus red mite, European red mite, etc.

Furthermore, the present compounds are also effective on insect pests which have increased resistance to the conventional insecticides and acaricides.

When the present compound is used as an active ingredient of insecticides and acaricides, it may be used without adding any other components, but, usually, it is mixed with solid carriers, liquid carriers, gaseous carriers, baits or the like or substrates such as porous ceramics sheets and nonwoven fabrics are impregnated with the compound. If necessary, with addition of surface active agents and other auxiliaries for formulation, the compound is used in the formulations of oil solution, emulsifiable concentrate, wettable powder, flowable, granule, dust, aerosol, fogging agent, smoking agent, poison bait, acaricidal sheet, and the like.

These formulations contain usually 0.01–95% by weight of the present compound as an active ingredient.

The solid carriers used for formulation include, for example, fine powders or granules of clays (such as kaolin clay, diatomaceous earth, synthetic silicon oxide, bentonite, Fubasamiclay and acid clay), talcs, ceramics, other inorganic minerals (such as sericite, quartz, sulfur, active carbon, calcium carbonate and hydrated silica), and chemical fertilizers (such as ammonium sulfate, ammonium phosphate, ammonium nitrate, urea and ammonium chloride). The liquid carriers include, for example, water, alcohols (such as methanol and ethanol), ketones (such as acetone and methyl ethyl ketone), aromatic hydrocarbons (such as benzene, toluene, xylene, ethylbenzene and methylnaphthalene), aliphatic hydrocarbons (hexane, cyclohexane, kerosene and light oil), esters (such as ethyl acetate and butyl acetate), nitriles (such as acetonitrile and isobutyronitrile), ethers (such as diisopropyl ether and dioxane), acid amides (such as N,N-dimethylformamide and N,N-dimethylacetamide), halogenated hydrocarbons (such as dichloromethane, trichloroethane and carbon tetrachloride), dimethyl sulfoxide, and vegetable oils such as soybean oil and cottonseed oil. The gaseous carriers, namely, propellants include, for example, Freon gas, butane gas, LPG (liquefied petroleum gas), dimethyl ether and carbon dioxide.

The surface active agents include, for example, alkylsulfate esters, alkylsulofonate salts, alkylarylsulfonate salts, alkylaryl ethers and polyoxyethylene compounds thereof, polyethylene glycol ethers, polyhydric alcohol esters and sugar alcohol derivatives.

The auxiliaries for formulation such as adhesive agents and dispersing agents include, for example, casein, gelatin, polysaccharides (such as starch powder, gum arabic, cellulose derivatives and alginic acid), lignin derivatives, bentonite, sugars, synthetic water-soluble polymers (such as polyvinyl alcohol, polyvinyl pyrrolidone and polyacrylic acids). Stabilizers include, for example, PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surface active agents and fatty acids or esters thereof.

The substrates for poisen baits include, for example, bait components such as grain powder, vegetable oil, sugar and crystalline cellulose, antioxidants such as dibutylhydroxytoluene and nordihydroguaiaretic acid, preservatives such as dehydroacetic acid, erroneous eating inhibitors such as Guinea pepper powder, and attractant flavor such as cheese flavor and onion flavor.

The thus obtained formulations are used as such or diluted with water. Furthermore, these formulations may be used alone or in admixture with other insecticides, nematicides, acaricides, fungicides, herbicides, plant growth regulating agents, synergists, fertilizers, soil improvers, animal feeds and the like.

Examples of the insecticides, nematicides and acaricides are as follows:

Organic phosphorous compounds such as fenitrothion [O,O-dimethyl O-(3-methyl-4-nitrophenyl) phosphorothioate], fention [O,O-dimethyl O-(3-methyl-4-(methylthio)phenyl)phosphorothioate], diazinon [O,O-diethyl-O-2-isopropyl-6-methylpyrimidine-4-ylphosphorothioate, chlorpyrifos [O,O-diethyl-O-3,5,6-trichloro-2-pyridylphosphorothioate], acephate [O,S-dimethylacetylphosphoramidothioate], methidathion [S-2,3-dihydro-5-methoxy-2-oxo-1,3,4-thiadiazol-3-ylmethyl O,O-dimethylphosphorodithioate], disulfoton [O,O-diethyl S-2-ethylthioethylphosphorodithioate], DDVP [2,2-dichlorovinyldimethylphosphate], sulprofos [O-ethyl O-4-(methylthio)phenyl S-propylphosphorodithioate], cyanophos [O-4-cyanophenyl O,O-dimethylphosphorothioate], dioxabenzofos [2-methoxy-4H-1,3,2-benzodioxaphosphorine-2-sulfide], dimethoate [O,O-dimethyl-S-(N-methylcarbamoylmethyl)dithiophosphate], phenthoate [ethyl 2-dimethoxyphosphinothioylthio(phenyl) acetate], malathion [diethyl(dimethoxyphosphinothioylthio) succinate], trichlorfon [dimethyl 2,2,2-trichloro-1-hydroxyethylphosphonate], azinphosmethyl [S-3,4-dihydro-4-oxo-1,2,3-benzotriazin-3-ylmethyl O,O-dimethylphosphoroditioate], monocrotophos [dimethyl(E)-1-methyl-2-(methylcarbamoyl)vinylphosphate], and ethion [O,O,O',O'-tetraethyl S,S'-methylenebis (phosphorodithioate)].

Carbamate compounds such as BPMC (2-sec-butylphenylmethylcarbamate), benfuracarb [ethyl N-[2,3-dihydro-2,2-dimethylbenzofuran-7-yloxycarbonyl(methyl) aminothio]-N-isopropyl-β-araninate], propoxur [2-isopropoxyphenyl N-methylcarbamate], carbosulfan [2,3-dihydro-2,2-dimethyl-7-benzo[b]furanyl N-dibutylaminothio-N-methylcarbamate], carbaryl [1-naphthyl-N-methylcarbamate], methomyl [S-methyl-N-[(methylcarbamoyl)oxy]thioacetoimidate], ethiofencarb [2-(ethylthiomethyl)phenylmethylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide], and fenothiocarb [S-(4-phenoxybutyl)-N,N-dimethylthiocarbamate].

Pyrethroid compounds such as ethofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS)-cis, trans-3-(2,2-dichlorovinyl)-2,2-dimethylcyclopropanecarboxylate], permethrin [3-phenoxybenzyl (1RS)-cis, trans-3-(2,2-dichlorovinyl)-2,2-dimethylcyclopropanecarboxylate], cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate (α-cyano-3-phenoxybenzyl N-(2-chloro-α,α,α-trifluoro-p-tolyl)-D-valinate), bifenthrin (2-methylbiphenyl-3-ylmethyl) (Z)-(1RS)-cis-3-(2-chloro-3,3,3-trifluoro-1-propenyl)-2,2-dimethylcyclopropanecarboxylate, 2-methyl-2-(4-bromodifluoromethoxyphenyl)propyl (3-phenoxybenzyl) ether, tralomethrin [(S)-α-cyano-3-phenoxybenzyl (1R-cis)3{(1'RS) (1',2',2',2'-tetrabromoethyl)}-2,2-dimethylcyclopropanecarboxylate], silafluofen [4-ethoxyphenyl {3-(4-fluoro-3-phenoxyphenyl)propyl}dimethylsilane], d-fenothrin [3-phenoxybenzyl (1R)-cis, trans)-chrysanthemate], cyphenothrin [(RS)-α-cyano-3-phenoxybenzyl (1R-cis, trans)-chrysanthemate], d-resmethrin [5-benzyl-3-furylmethyl (1R-cis, trans)-chrysanthemate], acrinathrin [(S)-α-cyano-3-phenoxybenzyl (1R-cis (Z))-(2,2-dimethyl-3-{oxo-3-(1,1,1,3,3,3-hexafluoropropyloxy)propenyl}cyclopropanecarboxylate], cyfluthrin [(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (1RS-cis (Z))-3-(2-chloro-3,3,3-trifluoroprop-1-enyl)-2,2-dimethylcyclopropanecarboxylate], transfluthrin [2,3,5,6-tetrafluorobenzyl (1R-trans)-3-(2,2-dichlorovinyl)-2,2-dimethylcyclopropanecarboxylate], tetramethrin [3,4,5,6-tetrahydrophthalimidomethyl (1RS)-cis, trans-chrysanthemate], allethrin [(RS)-3-allyl-2-methyl-4-oxocyclopent-2-enyl (1RS)-cis, trans-chrysanthemate], prallethrin [(S)-2-methyl-4-oxo-3-(2-propynyl)cyclopent-2-enyl (1R)-cis, trans-chrysanthemate], empenthrin [(RS)-1-ethynyl-2-methyl-2-pentenyl (1R)-cis, trans-chrysanthemate], imiprothrin [2,5-dioxo-3-(prop-2-ynyl)imidazolidin-1-ylmethyl (1R)-cis, trans-2,2-dimethyl-3-(2-methyl-1-propenyl)-cyclopropanecarboxylate], d-flamethrin [5-(2-propynyl)-furfuryl (1R)-cis, trans-chrysanthemate], and 5-(2-propynyl)furfuryl 2,2,3,3-tetramethylcyclopropanecarboxylate.

Thiadiazine derivatives such as buprofezin (2-tert-butylimino-3-isopropyl-5-phenyl-1,3,5-thiadiazin-4-one), nitroimidazolidine derivatives such as imidacloprid (1-(6-chloro-3-pyridylmethyl)-N-nitroimidazolidin-2-ylidenamine), neristoxin derivatives such as cartap (S,S'-(2-dimethylaminotrimethylene) bis(thiocarbamate), thiocyclam [N,N-dimethyl-1,2,3-trithian-5-ylamine] and bensultap [S,S'-2-dimethylaminotrimethylene di(benzenethiosulfonate)], N-cyanoamidine derivatives such as N-cyano-N'-methyl-N'-(6-chloro-3-pyridylmethyl) acetamidine, chlorinated hydrocarbon compounds such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane] and 1,1-bis (chlorophenyl)-2,2,2-trichloroethanol, benzoylphenylurea compounds such as chlorfluazuron [1-(3,5-dichloro-4-(3-chloro-5-trifluoromethylpyridin-2-yloxy)phenyl)-3-(2,6-difluorobenzoyl)urea], teflubenzuron [1-(3,5-dichloro-2,4-difluorophenyl)-3-(2,6-difluorobenzoyl)urea] and flufenoxuron [1-(4-(2-chloro-4-trifluoromethylphenoxy)-2-fluorophenyl)-3-(2,6-difluorobenzoyl)urea], formamidine derivatives such as amitraz [N,N'[(methylimino) dimethylidine] di-2,4-xylidine] and chlordimeform [N'-(4-chloro-2-methylphenyl)-N,N-dimethylmethanimidamide], thiourea derivatives such as diaphentiuron [N-(2,6-diisopropyl-4-phenoxyphenyl)-N'-tert-butylcarbodiimide], N-arylheterocyclic compounds methoxadiazon [5-methoxy-3-(2-methoxyphenyl)-1,3,4-oxadiazol-2-(3H)-one], bromopropylate [isopropyl 4,4'-dibromobenzylate], tetradifon [4-chlorophenyl 2,4,5-trichlorophenylsulfone], quinomethionate [S,S-6-methylquinoxaline-2,3-diyldithiocarbonate], propargite [2-(4-tert-butylphenoxy) cyclohexyl prop-2-yl sulfite], fenbutain-oxide [bis[tris(2-methyl-2-phenylpropyl)thiene]xodie], hexythiazox [(4RS, 5RS)-5-(4-chlorophenyl)-N-chlorohexyl-4-methyl-2-oxo-1, 3-thiazolidine-3-carboxamide], chlofentezin [3,6-bis(2-chlorophenyl)-1,2,4,5-tetrazine], pyridaben [2-tert-butyl-5-(4-tert-butylbenzylthio)-4-chloropyridazin-3(2H)-one], fenpyroximate [tert-butyl (E)-4-[(1,3-dimethyl-5-phenoxypyrazol-4-yl)methylenaminoxymethyl]benzoate], debfenpyrado [N-4-tert-butylbenzyl)-4-chloro-3-ethyl-1-methyl-5-pyrazolecarboxamide], polynactins complex [tetranactin, dinactin, trinactin], pirimidiphen [5-chloro-N-[2-{4-(2-ethoxyethyl)-2,3-dimethylphenoxy}ethyl]-6-ethylpyrimidin-4-amine, milmectin, abamectin, ibamectin, and azadilactin [AZAD].

The present compounds in an effective amount are applied to the places, for example, crops where insects and mites and insects or mites inhabit or will inhabit.

When the present compounds are used as agricultural insecticides or acaricides, the amount of the compounds applied is usually 0.1–100 g per 10 ares. In the case of emulsifiable concentrate, wettable powder, flowable, or the like which is diluted with water, the application concentration is usually 1–10000 ppm, and granule or dust is applied as it is without dilution. When the present compounds are used as epidemic preventing insecticides or acaricides, emulsifiable concentrate, wettable powder and flowable are usually diluted to 0.1–500 ppm with water and oil solution, aerosol, poison bait, fogging agent and acaricidal sheet are used as they are.

The application amount and application concentration vary depending on the kind of formulations, the application time, the application place, the application method, the kind of insect pests, the state of damage, etc., and can be increased or decreased irrespective of the above-mentioned ranges.

The present invention will be explained in more detail by the following nonlimiting preparation examples, formulation examples and test examples.

First, the preparation examples of the present compounds are shown below.

PREPARATION EXAMPLE 1

[Preparation example of the present compound (1)]

3,5-Dichloro-4-fluorobenzotrifluoride (0.93 g, 4 mmols) and 60% oily sodium hydride (0.16 g, 4 mmols) were added in succession to a suspension of 3,3'-di(5-amino-1,2,4-triazolyl) disulfide (0.46 g, 2 mmols) in N,N-dimethylforamide (8 ml) under ice cooling. The mixture was stirred at room temperature for 12 hours and, then, transferred to a pressure vessel. The content was cooled to lower than −20° C. and thereto were added iodotrifluoromethane (0.78 g, 4 mmols), sodium hydroxymethanesulfinate dihydrate (0.92 g, 5 mmols) and water (0.4 ml). After the vessel was closed, the content was further stirred at room temperature for 12 hours. The reaction mixture was poured into water and extracted with ethyl acetate. The organic layer was washed with saturated aqueous sodium chloride solution and dried over anhydrous magnesium sulfate. The residue obtained by concentration under reduced pressure was subjected to silica gel column chromatography (elution solvent; n-hexane:ethyl acetate =3:1) to obtain a mixture of 5-amino-1-(2,6-dichloro-4-trifluoromethylphenyl)-3-trifluoromethylsulfenyl-1,2,4-triazole and 5-amino-1-(2,6-dichloro-4-trifluoromethylphenyl)-3-(2,6-dichloro-4-trifluoromethylphenylsulfenyl-1,2,4-triazole. The mixture was further subjected to recycling preparative HPLC (high performance liquid chromatography; LC-908 manufactured by Japan Analytical Industry Co., Ltd.; elution solvent: chloroform) to obtain first 5-amino-1-(2,6-dichloro-4-trifluoromethylphenyl)-3-(2,6-dichloro-4-trifluoromethylphenylsulfenyl-1,2,4-triazole which was a by-product.

$^1$H-NMR (250 MHz, CDCl$_3$/TMS): δ (ppm)=7.77 (s,2H), 7.68 (s,2H), 4.68 (brs,2H).

Furthermore, elution with chloroform was carried out to obtain 0.26 g of 5-amino-1-(2,6-dichloro-4-trifluoromethylphenyl)-3-trifluoromethylsulfenyl-1,2,4-triazole which is the desired present compound.

m.p. 166° C. $^1$H-NMR (250 MHz, CDCl$_3$/TMS): δ (ppm) =7.80 (s,2H), 5.38 (s,2H).

PREPARATION EXAMPLE 2

[Preparation example of the present compound (2)]

In a pressure vessel were charged 3,3'-di[1-(2,6-dichloro-4-trifluoromethylphenyl)-1,2,4-triazolyl] disulfide (1.66 g, 2.65 mmols) prepared in the Referential Preparation Example 1 given hereinafter, iodotrifluoromethane (1.04 g, 5.3 mmols), sodium hydroxymethanesulfinate dihydrate (1.02 g, 6.63 mmols), N,N-dimethylforamide (11 ml) and water (0.55 ml) at lower than −20° C. After the vessel was closed, the content was stirred at room temperature for 12 hours. The reaction mixture was poured into water and extracted with ethyl acetate. The organic layer was washed with saturated aqueous sodium chloride solution and dried over anhydrous magnesium sulfate. The residue obtained by concentration under reduced pressure was subjected to silica gel column chromatography to obtain 1.30 g of 1-(2,6-dichloro-4-trifluoromethylphenyl)-3-trifluoromethylphenylsulfenyl-1,2,4-triazole.

m.p. 51° C. $^1$H-NMR (250 MHz, CDCl$_3$/TMS): δ (ppm) =8.36 (s,1H), 7.80 (s,2H).

PREPARATION EXAMPLE 3

[Preparation example of the present compound (3)]

The present compound (1) (100 mg, 0.25 mmol) was dissolved in chloroform (2 ml), and 70% m-chloroperbenzoic acid (62 mg, 0.25 mmol) was added to the resulting solution at room temperature. After stirring at room temperature for 12 hours, the content was diluted with ethyl acetate and washed with saturated aqueous sodium bicarbonate solution, 10% aqueous sodium sulfite solution and saturated aqueous sodium bicarbonate solution in succession. The organic layer was dried over anhydrous magnesium sulfate and, then, concentrated. The resulting residue was subjected to silica gel column chromatography to obtain 13 mg of 5-amino-1-(2,6-dichloro-4-trifluoromethylphenyl)-3-trifluoromethylsulfonyl-1,2,4-triazole.

m.p. 174°–176° C. $^1$H-NMR (250 MHz, CDCl$_3$/TMS): δ (ppm)=7.83 (s,2H), 6.20 (s,2H).

PREPARATION EXAMPLE 4

[Preparation example of the present compound (8)]

A mixture of the present compound (1) (110 mg, 0.3 mmol), vanillin (46 mg, 0.3 mmol), p-toluenesulfonic acid monohydrate (5 mg) and toluene (25 ml) was heated at reflux with removing water by Dean-Stark apparatus for 6 hours. After cooling, the mixture was concentrated under reduced pressure and the obtained residue was subjected to silica gel column chromatography to obtain 84 mg of 1-(2,6-dichloro-4-trifluoromethylphenyl)-5-[N-(4-hydroxy-3-methoxybenzylidene)]amino-3-trifluoromethylsulfenyl-1,2,4-triazole.

Property: Resinous $^1$H-NMR (250 MHz, CDCl$_3$/TMS): δ (ppm)=9.23 (s,1H), 7.80 (s,2H), 7.43 (dd, J=9, 3Hz, 1H), 7.36 (d, J=3Hz, 1H), 6.98 (d, J=9Hz, 1H), 6.35 (brs, 1H), 3.90 (s,3H).

PREPARATION EXAMPLE 5

[Preparation example of the present compound (9)]

A mixture of the present compound (1) (0.40 g, 1 mmol), trimethylacetaldehyde (0.43 g, 5 mmols), p-toluenesulfonic acid monohydrate (17 mg) and toluene (10 ml) was heated at reflux with removing water by Dean-Stark apparatus for 3 hours. After cooling, the mixture was concentrated under reduced pressure, and methanol (10 ml) was added thereto. This mixture was stirred at room temperature for 12 hours and concentrated under reduced pressure. The obtained residue was subjected to silica gel chromatography to give 0.19 g of 1-(2,6-dichloro-4-trifluoromethylphenyl)-5-(2,2-dimethyl-1-methoxypropyl)amino-3-trifluoromethylsulfenyl-1,2,4-triazole.

$n_D^{24.8}$ 1.4880 $^1$H-NMR (250 MHz, CDCl$_3$/TMS): δ (ppm)=7.81 (s,1H), 4.93 (d; J=10Hz, 1H), 4.09 (d; J=10Hz, 1H), 3.39 (s, 3H), 0.94 (s, 9H).

PREPARATION EXAMPLE 6

[Preparation example of the present compound (10)]

A mixture of the present compound (1) (0.31 g, 0.79 mmol), triethyl orthopropionate (0.83 g, 4.7 mmols) and p-toluenesulfonic acid monohydrate (13 mg) was heated at 80° C. for 3 hours. After cooling, the mixture was concentrated and the residue was subjected to silica gel chromatography to give 0.36 g of 1-(2,6-dichloro-4-trifluoromethylphenyl)-5-(1-ethoxypropylidene)amino-3-trifluoromethylsulfenyl-1,2,4-triazole.

$n_D^{23.9}$ 1.4973 $^1$H-NMR (250 MHz, CDCl$_3$/TMS): δ (ppm)=7.73 (s,2H), 4.01 (q; J=7.5Hz, 2H), 2.81 (q; J=7.5Hz, 2H), 1.19 (t; 7.5Hz, 3H), 1.16 (t; J=7.5Hz, 3H).

PREPARATION EXAMPLE 7

[Preparation example of the present compound (11)]

The present compound (10) (0.26 g, 0.55 mmol) obtained in Preparation Example 6 was dissolved in 99.5% ethanol (10 ml) and thereto was added, little by little, sodium borohydride (0.10 g, 2.6 mmols) at room temperature with stirring. The mixture was stirred at room temperature for 4 hours and, then, concentrated. The residue was extracted with ethyl acetate and washed with water. The organic layer was dried over anhydrous magnesium sulfate and, then, concentrated under reduced pressure to give an oily product. This was subjected to silica gel chromatography to give 0.23 g of 1-(2,6-dichloro-4-trifluoromethylphenyl)-5-propylamino-3-trifluoromethylsulfenyl-1,2,4-triazole.

m.p. 84.1° C. $^1$H-NMR (250 MHz, CDCl$_3$/TMS): δ (ppm)=7.78 (s,2H), 4.00 (brt; J=7.0Hz, 1H), 3.42 (dt; J=7.0Hz, J=7.0Hz, 2H), 1.63 (tq.; J=7.0Hz, J=7.0Hz, 2H), 0.94 (t; J=7.0Hz, 3H).

PREPARATION EXAMPLE 8

[Preparation example of the present compound (12)]

The present compound (1) (1.19 g, 3 mmols) was dissolved in bromoform (10 ml), and thereto was added dropwise tert-butyl nitrite (0.93 g, 9 mmols) at 80° C. After stirring at 80° C. for 1 hour, the mixture was concentrated under reduced pressure. The obtained residue was subjected to silica gel chromatography to give 0.90 g of 1-(2,6-dichloro-4-trifluoromethylphenyl)-5-bromo-3-trifluoromethylsulfenyl-1,2,4-triazole.

$n_D^{28.8}$ 1.5224 $^1$H-NMR (300 MHz, CDCl$_3$/TMS): δ (ppm)=7.81 (s,2H).

PREPARATION EXAMPLE 9

[Preparation example of the present compound (13)]

The present compound (12) (0.30 g, 0.63 mmol) obtained in Preparation Example 8 and diethylamine (5 ml) were charged in a pressure vessel, and the mixture was continuously heated at 80° C. for 12 hours with stirring. After cooling, the content was concentrated, and the residue was subjected to silica gel chromatography to give 0.19 g of 1-(2,6-dichloro-4-trifluoromethylphenyl)-5-diethylamino-3-trifluoromethylsulfenyl-1,2,4-triazole.

m.p. 74.2° C. $^1$H-NMR (250 MHz; CDCl$_3$/TMS): δ (ppm)=7.75 (s,2H), 3.23 (q; J=7.0 Hz, 4H), 1.04 (t; J=7.0Hz, 6H).

PREPARATION EXAMPLE 10

[Preparation example of the present compound (14)]

Acetyl chloride (87 mg, 1.1 mmol) was added dropwise to a mixture of the present compound (1) (0.40 g, 1 mmol), triethylamine (0.11 g, 1.1 mmol) and toluene (20 ml) at room temperature. After stirring at room temperature for 6 hours, the mixture was poured into water and extracted with ethyl acetate. The organic layer was dried over anhydrous magnesium sulfate and concentrated under reduced pressure. The residue was subjected to silica gel chromatography to give 0.35 g of 1-(2,6-dichloro-4-trifluoromethyl-phenyl)-5-acetylamino-3-trifluoromethylsulfenyl-1,2,4-triazole.

m.p. 154.2° C. $^1$H-NMR (250 MHz; CDCl$_3$/TMS): δ (ppm)=9.95 (br.s,1H), 7.76 (s,2H), 2.24 (s, 3H).

PREPARATION EXAMPLE 11

[Preparation example of the present compound (15)]

Sixty percent oily sodium hydride (40 mg, 1 mmol) was added to a solution of 1-(2,6-dichloro-4-trifluoromethylphenyl)-3-mercapto-1,2,4-triazole 0.31 g, 1 mmol) in N,N-dimethylformamide (10 ml) at room temperature in a nitrogen atmosphere. After stirring at room temperature for 15 minutes, the atmosphere in the reaction vessel (20 ml volume) was replaced with tetrafluoroethylene gas, and the mixture was heated at 80° C. for 1 hour. The mixture was poured into water and extracted with ethyl acetate. The organic layer was dried over anhydrous magnesium sulfate and concentrated under reduced pressure. The obtained oily product was subjected to silica gel chromatography to give 0.21 g of 1-(2,6-dichloro-4-trifluoromethylphenyl)-3-(1,1,2,2-tetrafluoroethyl)-1,2,4-triazole.

$n_D^{25.8}$ 1.4952 $^1$H-NMR (250 MHz; CDCl$_3$/TMS): δ (ppm)=8.35 (s,1H), 7.80 (s,2H), 6.23 (tt; J=54Hz, J=4.3Hz, 1H).

PREPARATION EXAMPLE 12

[Preparation example of the present compound (47)]

Sodium hydroxide (3.3 g) was added to a mixture of 1-(2,6-dichloro-4-trifluoromethylphenyl)-3-mercapto-1,2,4-triazole (0.32 g, 1 mmol), 1,4-dioxane (13 ml) and water (13 ml) at one time with blowing thereinto chlorodifluoromethane gas. The temperature rose to 60°–70° C. After the rise of temperature stopped, the mixture was cooled to room temperature and poured into water. Ethyl acetate was added and the organic layer was separated and washed with saturated aqueous sodium chloride solution. The organic layer was dried over anhydrous magnesium sulfate and concentrated under reduced pressure. The obtained residue was subjected to silica gel chromatography to give 0.29 g of 1-(2,6-dichloro-4-trifluoromethylphenyl)-3-difluoromethylsulfenyl-1,2,4-triazole.

$n_D^{23.8}$ 1.5203 $^1$H-NMR (250 MHz; CDCl$_3$/TMS): δ (ppm)=8.28 (s,1H), 7.79 (s,2H), 7.50 (t; J=56Hz, 1H).

PREPARATION EXAMPLE 13

[Preparation example of the present compound (39)]

The procedure of Preparation Example 1 was repeated except that 0.98 g of iodopentafluoroethane was used in place of 0.78 g of iodotrifluoromethane, thereby to obtain 1.04 g of 5-amino-1-(2,6-dichloro-4-trifluoromethylphenyl)-3-pentafluoroethylsulfenyl-1,2,4-triazole.

m.p. 133.9° C. $^1$H-NMR (250 MHz; CDCl$_3$/TMS): δ (ppm)=7.80 (s,2H), 5.89 (br. s,2H).

PREPARATION EXAMPLE 14

[Preparation example of the present compound (6)]

The procedure of Preparation Example 1 was repeated except that 0.40 g of 3,3'-di(1,2,4-triazolyl) disulfide was used in place of 0.46 g of 3,3'-di(5-amino-1,2,4-triazolyl) disulfide and 0.86 g of 2,3-dichloro-5-trifluoromethylpyridine was used in place of 0.93 g of 3,5-dichloro-4-fluorobenzotrifluoride (the recycling HPLC was not needed), thereby to obtain 0.86 g of 1-(3-chloro-5-trifluoromethylpyridin-2-yl)-3-trifluoromethylsulfenyl-1,2,4-triazole.

m.p. 40° C. $^1$H-NMR (250 MHz; CDCl$_3$/TMS): δ (ppm) =8.98 (s,1H), 8.74 (d; J=2.2Hz, 1H), 8.24 (d; J=2.2Hz, 1H).

PREPARATION EXAMPLE 15

[Preparation example of the present compound (48)]

A mixture of the present compound (47) (0.14 g, 0.38 mmol), 80% m-chloroperbenzoic acid (82 mg, 0.38 mmol)

and chloroform (5 ml) was stirred for 12 hours at room temperature. The reaction mixture was washed in succession with 10% aqueous sodium sulfite solution, saturated aqueous sodium bicarbonate solution and saturated aqueous sodium chloride solution. The organic layer was dried over anhydrous magnesium sulfate and concentrated under reduced pressure. The obtained residue was subjected to silica gel chromatography to give 0.12 g of 1-(2,6-dichloro-4-trifluoromethylphenyl)-3-difluoromethylsulfinyl-1,2,4-triazole.

m.p. 129.5° C. $^1$H-NMR (250 MHz; CDCl$_3$/TMS): δ (ppm)=8.49 (s,1H), 7.83 (s,2H), 6.84 (t; J=55Hz, 1H).

Examples of the present compounds are shown in Table 2 together with properties thereof.

TABLE 2

| Compound No. | $X^1$ | Y | $R^1$ | $R^5$ | n | Physical properties |
|---|---|---|---|---|---|---|
| (1) | Cl | CCl | NH$_2$ | CF$_3$ | 0 | m.p. 166° C. |
| (2) | Cl | CCl | H | CF$_3$ | 0 | m.p. 51° C. |
| (3) | Cl | CCl | NH$_2$ | CF$_3$ | 2 | m.p. 174–176° C. |
| (4) | Cl | CCl | CH$_3$ | CF$_3$ | 0 | $n_D^{21.3}$ 1.4951 |
| (5) | Cl | N | CH$_3$ | CF$_3$ | 0 | $n_D^{21.3}$ 1.4884 |
| (6) | Cl | N | H | CF$_3$ | 0 | m.p. 40° C. |
| (7) | Cl | CCl | H | CF$_3$ | 2 | m.p. 69.8° C. |
| (8) | Cl | CCl | *1) | CF$_3$ | 0 | Resinous |
| (9) | Cl | CCl | NHCH(OCH$_3$)t-Bu | CF$_3$ | 0 | $n_D^{24.8}$ 1.4880 |
| (10) | Cl | CCl | N=C(OCH$_2$CH$_3$)(CH$_2$CH$_3$) | CF$_3$ | 0 | $n_D^{29.9}$ 1.4973 |
| (11) | Cl | CCl | NHCH$_2$CH$_2$CH$_3$ | CF$_3$ | 0 | m.p. 84.1° C. |
| (12) | Cl | CCl | Br | CF$_3$ | 0 | $n_D^{28.8}$ 1.5224 |
| (13) | Cl | CCl | N(CH$_2$CH$_3$)$_2$ | CF$_3$ | 0 | m.p. 74.2° C. |
| (14) | Cl | CCl | NHCOCH$_3$ | CF$_3$ | 0 | m.p. 154.2° C. |
| (15) | Cl | CCl | H | CF$_2$CF$_2$H | 0 | $n_D^{25.8}$ 1.4952 |
| (16) | NO$_2$ | CCl | H | CF$_3$ | 0 | m.p. 48.2° C. |
| (17) | Cl | CCl | NH$_2$ | CH$_2$CF$_3$ | 0 | m.p. 108.0° C. |
| (18) | F | CCl | NH$_2$ | CF$_3$ | 0 | m.p. 168.0° C. |
| (19) | Cl | CCl | N(CH$_2$CH$_3$)COCH$_3$ | CF$_3$ | 0 | $n_D^{25.3}$ 1.5017 |
| (20) | Cl | CCl | N(COCH$_2$CH$_3$)$_2$ | CF$_3$ | 0 | m.p. 75.7° C. |
| (21) | Cl | CCl | N=C(CH$_3$)(OCH$_2$CH$_3$) | CF$_3$ | 0 | oil |

$^1$HMR(250MH$_z$, CDCl$_3$/TMS: δ(ppm) = 7.73(s, 2H), 4.01(q:J=7.1Hz, 2H) 2.40(s, 3H), 1.17(t:J=7.1Hz, 3H)

| (22) | Cl | CCl | pyrrolyl (N-linked) | CF$_3$ | 0 | $n_D^{24.3}$ 1.5339 |
| (23) | Cl | CCl | NHCH$_2$CH$_3$ | CF$_3$ | 0 | m.p. 129.4° C. |
| (24) | Cl | CCl | NHCH$_3$ | CF$_3$ | 0 | m.p. 119.8° C. |
| (25) | Cl | CCl | N=CCH$_3$N(CH$_3$)$_2$ | CF$_3$ | 0 | Resinous |
| (26) | Cl | CCl | pyrrolidinyl (N-linked) | CF$_3$ | 0 | m.p. 102.0° C. |
| (27) | Cl | CCl | N(CH$_3$)CH$_2$CH$_3$ | CF$_3$ | 0 | $n_D^{25.2}$ 1.5034 |
| (28) | Cl | CCl | NHCH(CH$_3$)CH$_2$CH$_3$ | CF$_3$ | 0 | Resinous |
| (29) | Cl | CCl | morpholinyl (N-linked) | CF$_3$ | 0 | m.p. 88.8° C. |
| (30) | Cl | CCl | piperidinyl (N-linked) | CF$_3$ | 0 | $n_D^{26.6}$ 1.5098 |
| (31) | Cl | CCl | NH(CH$_2$)$_3$CH$_3$ | CF$_3$ | 0 | Resinous |
| (32) | Cl | CCl | NHCH(CH$_3$)$_2$ | CF$_3$ | 0 | m.p. 87.2° C. |
| (33) | Cl | CCl | NHCH$_2$CH(CH$_3$)$_2$ | CF$_3$ | 0 | Resinous |
| (34) | F | CCl | NHCH(OCH$_3$)t-Bu | CF$_3$ | 0 | $n_D^{26.4}$ 1.4613 |
| (35) | Cl | CCl | H | CF$_2$CF$_3$ | 0 | m.p. 50.1° C. |

TABLE 2-continued

| | $X^1$ | Y | $R^3$ | $R^5$ | n | Physical properties |
|---|---|---|---|---|---|---|
| (36) | Cl | CCl | NH—△ | $CF_3$ | 0 | m.p. 130.1° C. |
| (37) | Cl | CCl | $NHCH_2C(CH_3)_3$ | $CF_3$ | 0 | $n_D^{24.6}$ 1.4941 |
| (38) | Cl | CCl | $NH(CH_2)_3OCH_3$ | $CF_3$ | 0 | m.p. 129.3° C. |
| (39) | Cl | CCl | $NH_2$ | $CF_2CF_3$ | 0 | m.p. 133.9° C. |
| (40) | Cl | CCl | $NHC(CH_3)_3$ | $CF_3$ | 0 | oil |
| | | | $^1$H-NMR(300MHz, CDCl$_3$/TMS): δ(ppm) = 7.77(s, CF$_3$2H), 1.44(s, 9H) | | | |
| (41) | Cl | CCl | NH—◇ | $CF_3$ | 0 | $n_D^{24.7}$ 1.5081 |
| (42) | Cl | CCl | NH—(tetrahydropyran) | $CF_3$ | 0 | Resinous |
| (43) | Cl | CCl | $NHCH(OC_2H_5)C(CH_3)_3$ | $CF_3$ | 0 | $n_D^{23.6}$ 1.4913 |
| (44) | Cl | CCl | $NHCH(SCH_2CH_3)$t-Bu | $CF_3$ | 0 | m.p. 77.5° C. |
| (45) | Cl | CCl | $N(CO_2CH_2CH_3)_2$ | $CF_3$ | 0 | $n_D^{24.7}$ 1.4877 |
| (46) | Cl | CCl | $NHCH_2OCH_3$ | $CF_3$ | 0 | $n_D^{23.2}$ 1.5123 |
| (47) | Cl | CCl | H | $CF_2H$ | 0 | $n_D^{23.8}$ 1.5203 |

| Compound No. | $X^1$ | Y | $R^3$ | $R^5$ | n | Physical properties |
|---|---|---|---|---|---|---|
| (48) | Cl | CCl | H | $CF_2H$ | 1 | m.p. 129.5° C. |
| (49) | Cl | CCl | $NH_2$ | $CF_2H$ | 0 | m.p. 135.4° C. |
| (50) | Cl | CCl | $N=CHN(CH_3)_2$ | $CF_2H$ | 0 | m.p. 108.4° C. |
| (51) | Cl | CCl | $NH_2$ | $CF_2H$ | 1 | m.p. 204.4° C. |
| (52) | Cl | CCl | $NH_2$ | $CF_2CF_2H$ | 0 | m.p. 142.3° C. |
| (53) | Cl | CCl | H | $CF_2Br$ | 0 | m.p. 53.1° C. |
| (54) | Cl | CCl | $NH_2$ | $CF_2Br$ | 0 | m.p. 216.4° C. |
| (55) | Cl | CCl | NH—(2,6-dichloro-4-trifluoromethylphenyl) | $CF_3$ | 0 | m.p. 138.1° C. |
| (56) | Cl | CCl | $N(CO_2CH_2CH_2CH_3CH_3)_2$ | $CF_3$ | 0 | $n_D^{21.7}$ 1.4790 |
| (57) | Cl | CCl | $N=CH$—(4-butylphenyl)—$(CH_2)_3CH_3$ | $CF_3$ | 0 | $n_D^{24.0}$ 1.5530 |
| (58) | Cl | CCl | $NHCH_2OCH_2CH_3$ | $CF_3$ | 0 | $n_D^{23.7}$ 1.5150 |
| (59) | Cl | CCl | $NHCOCH_2OCH_3$ | $CF_3$ | 0 | resinous |
| (60) | Cl | CCl | $NHS(CH_2)_3CH_3$ | $CF_3$ | 0 | m.p. 73.2° C. |
| (61) | Cl | CCl | $N(CO_2CH_2CH_2CH_3)_2$ | $CF_3$ | 0 | $n_D^{24.6}$ 1.4812 |
| (62) | Cl | CCl | $N[CO_2CH(CH_3)_2]_2$ | $CF_3$ | 0 | $n_D^{24.8}$ 1.4748 |
| (63) | Cl | CCl | $NCO_2CH(CH_3)_2$ | $CF_3$ | 0 | $n_D^{24.9}$ 1.4898 |
| (64) | Cl | CCl | $NHCOCH_2C(CH_3)_3$ | $CF_3$ | 0 | m.p. 166.2° C. |
| (65) | Cl | CCl | thiomorpholino (N—S ring) | $CF_3$ | 0 | $n_D^{24.1}$ 1.5405 |
| (66) | Cl | CCl | $NHSCH(CH_3)_2$ | $CF_3$ | 0 | m.p. 94.3° C. |
| (67) | Cl | CCl | $NHSN[CH(CH_3)_2]CH_2$—$CH_2CO_2CH_2CH_3$ | $CF_3$ | 0 | m.p. 96.3° C. |
| (68) | Cl | CCl | $N(SO_2CH_3)_2$ | $CF_3$ | 0 | m.p. 134.0° C. |

TABLE 2-continued

| | | | | | | |
|---|---|---|---|---|---|---|
| (69) | Cl | CCl | [4-Cl, 2-NO₂, 5-CF₃-phenyl-NH-] | CF₃ | 0 | m.p. 117.6° C. |
| (70) | Cl | CCl | [4-Cl, 2-CF₃, 5-NO₂-phenyl-NH-] | CF₃ | 0 | m.p. 137.7° C. |
| (71) | Cl | CCl | NHCH₂SCH₃ | CF₃ | 0 | m.p. 85.4° C. |
| (72) | Cl | CCl | (thiazolidin-3-yl) | CF₃ | 0 | m.p. 96.4° C. |
| (73) | Cl | CCl | NHSN(CH₃)CO₂CH₂CH₃ | CF₃ | 0 | m.p. 119.6° C. |
| (74) | Cl | CCl | NHSN(CH₂CH₂CH₂CH₃)₂ | CF₃ | 0 | $n_D^{21.3}$ 1.5010 |
| (75) | Cl | CCl | NHSCO₂CH₃ | CF₃ | 0 | m.p. 136.5° C. |
| (76) | Cl | CCl | N(COSCH₂CH₃)₂ | CF₃ | 0 | $n_D^{21.3}$ 1.5260 |

*1) 4-Hydroxy-3-methoxybenzylideneaminis group

Preparation examples of disulfide compounds [2] which are intermediates in preparing the present compounds are shown below.

Referential Preparation Example 1

Sixty percent oily sodium hydride (0.44 g, 11 mmols) was added to a mixture of 3,3'-di(1,2,4-triazolyl) disulfide (1.11 g, 5.55 mmols), 3,5-dichloro-4-fluorobenzotrifluoride (2.59 g, 11.1 mmols) and N,N-dimethylformamide (25 ml) at one time at 0° C. After stirring for 1 hour under at 0° C., the mixture was further stirred for 12 hours at room temperature. The reaction mixture was poured into water and extracted with ethyl acetate. The organic layer was washed with saturated aqueous sodium chloride solution, dried over anhydrous magnesium sulfate and concentrated under reduced pressure. The obtained residue was subjected to silica gel chromatography to give 3.13 g of 3,3'-di[1-(2,6-dichloro-4-trifluoromethylphenyl)-1,2,4-triazolyl] disulfide as a crystal.

¹H-NMR (250 MHz; CDCl₃/TMS): δ (ppm)=8.27 (s,2H), 7.75 (s,4H).

Other examples of the disulfide compounds represented by the-formula [2] which are intermediates in preparing the present compounds are shown below together with ¹H-NMR data.

3,3'-Di[1-(2,6-dichloro-4-trifluoromethylphenyl)-5-methyl-1,2,4-triazolyl] disulfide ¹H-NMR (250 MHz; CDCl₃/TMS): δ (ppm)=7.75 (s,4H), 2.32 (s,6H).

3,3'-Di[1-(3-chloro-5-trifluoromethyl-2-pyridyl)-1,2,4-triazolyl] disulfide

¹H-NMR (250 MHz; CDCl₃/TMS): δ (ppm)=8.76 (d, J=2Hz, 2H), 8.20 (d, J=2Hz, 2H), 2.53 (s,6H).

3,3'-Di[1-(2,6-dichloro-4-trifluoromethylphenyl)-5-amino-1,2,4-triazolyl] disulfide ¹H-NMR (250 MHz; CDCl₃/TMS): δ (ppm)=7.68 (s,4H), 5.72 (br. s,4H).

Formulation examples are shown below, where parts are by weight and the present compounds used are indicated by the numbers given in Table 2.

Formulation Example 1 Emulsifiable concentrate

Ten parts of each of the present compounds (1)–(76) was dissolved in 35 parts of xylene and 35 parts of dimethylformamide. To the solution were added 14 parts of polyoxyethylenestyrylphenyl ether and 6 parts of calcium dodecylbenzenesulfonate, followed by thorough stirring and mixing to obtain a 10% emulsifiable concentrate of each compound.

Formulation Example 2 Wettable powder

Twenty parts of each of the present compounds (1)–(76) was added to a mixture comprising 4 parts of sodium laurylsulfate, 2 parts of calcium lignin sulfonate, 20 parts of synthetic hydrous silicon oxide fine powder and 54 parts of diatomaceous earth, followed by stirring and mixing by a juice mixer to obtain a 20% wettable powder of each compound.

Formulation Example 3 Granule

Five parts of synthetic hydrous silicon oxide fine powder, 5 parts of sodium dodecylbenzenesulfonate, 30 parts of bentonite and 55 parts of clay were added to each of the present compounds (1)–(76), followed by thorough stirring and mixing. A suitable amount of water was added to the resulting mixture. This was further stirred, granulated by a granulator and air dried to obtain a 5% granule of each compound.

Formulation Example 4 Dust

One part of each of the present compounds (1)–(76) was dissolved in a suitable amount of acetone. To the solution were added 5 parts of synthetic hydrous silicon oxide fine powder, 0.3 part of PAP and 93.7 parts of clay, followed by stirring and mixing by a juice mixer. Acetone was removed by evaporation to obtain a 1% dust of each compound.

Formulation Example 5 Flowable

Twenty parts of each of the present compounds (1)–(76) and 1.5 part of sorbitan trioleate were mixed with 28.5 parts of an aqueous solution containing 2 parts of polyvinyl alcohol. The mixture was finely ground by a sand grinder (3 μ or less in particle diameter) and, then, thereto were added 0.05 part of xanthane gum and 40 parts of an aqueous solution containing 0.1 part of aluminum magnesium silicate and further added 10 parts of propylene glycol, followed by stirring and mixing to obtain a 20% flowable agent of each compound.

Formulation Example 6 Oil solution 0.1 Part of each of the present compounds (1)–(76) was dissolved in 5 parts of xylene and 5 parts of trichloroethane, and the solution was mixed with 89.9 parts of deodorized kerosene to obtain a 0.1% oil solution of each compound.

Formulation Example 7 Oily aerosol 0.1 Part of each of the present compounds (1)–(76), 0.2 part of tetramethrin, 0.1 part of d-fenothrin, 10 parts of trichloroethane and 59.6 parts of deodorized kerosene were mixed to dissolve the ingredients, and the solution was charged in an aerosol container, to which a valve part was fitted. Then, 30 parts of a propellant (liquefied petroleum gas) was charged under pressure through the valve part to obtain an oily aerosol of each compound.

Formulation Example 8 Aqueous aerosol 0.2 Part of each of the present compounds (1)–(76), 0.2 part of d-allethrin, 0.2 part of d-fenothrin, 5 parts of xylene, 3.4 parts of deodorized kerosene and 1 part of an emulsifier (ATMOS 300 manufactured by Atlas Chemical Co., Ltd.) were mixed to dissolve the ingredients. The solution and 50 parts of pure water were charged in an aerosol container, to which a valve part was fitted. Then, 40 parts of a propellant (liquefied petroleum gas) was charged under pressure through the valve part to obtain an aqueous aerosol of each compound.

Formulation Example 9 Mosquito coil 0.3 Gram of d-allethrin was added to 0.3 g of each of the present compounds (1)–(76) and the mixture was dissolved in 20 ml of acetone. The solution was uniformly stirred and mixed with 99.4 g of a carrier for mosquito coil (a mixture of camphor powder:lees powder:wood meal at 4:3:3). Thereto was added 120 ml of water and the mixture was well kneaded, followed by shaping and drying to obtain a mosquito coil of each compound.

Formulation Example 10 Electric mosquito-repellent mat

Acetone was added to 0.4 g of each of the present compounds (1)–(76), 0.4 g of d-allethrin and 0.4 g of pipenyl butoxide to dissolve the ingredients to prepare a solution in an amount of 10 ml in total. A substrate for electric mat (fibrils of a mixture of cotton linter and pulp which were hardened into a sheet) of 2.5 cm×1.5 cm×0.3 cm thick was uniformly impregnated with the above solution to obtain an electric mosquito-repellent mat containing each compound.

Formulation Example 11 Heat smoking agent 100 mg of each of the present compounds (1)–(76) was dissolved in a suitable amount of acetone. A porous ceramic sheet of 4.0 cm×4.0 cm×1.2 cm thick was impregnated with the resulting solution to obtain a heat smoking agent containing each compound.

Formulation Example 12 Poison bait 10 mg of each of the present compounds (1)–(76) was dissolved in 0.5 ml of acetone. The solution was uniformly mixed with 5 g of a solid feed powder for animals (solid feed powder for breeding: CE-2 manufactured by Japan Kurea Co., Ltd.). Then, acetone was removed by air drying to obtain a 0.5% poison bait of each compound.

Formulation Example 13 Mite-repellent sheet

Each of the present compounds (1)–(76) was diluted with acetone and was dripped onto a nonwoven fabric so that the fabric was impregnated with 1 g/m$^2$ of the compound. Acetone was removed by air drying to obtain a mite-repellent sheet.

Formulation Example 14 Mite-repellent sheet

Each of the present compounds (1)–(76) was diluted with acetone and dripped onto a filter paper so that the filter paper was impregnated with 1 g/m$^2$ of the compound. Acetone was removed by air drying to obtain a mite-repellent sheet.

The following test examples show that the present compounds are useful as active ingredients of insecticides and acaricides. The present compounds used are indicated by the numbers given in Table 2 and the compounds used for comparison are shown by the numbers given in Table 3.

TABLE 3

| Chemical structure formula | Notes |
|---|---|
| (A) [structure: 2,6-dichloro-4-trifluoromethylphenyl group attached to N-N ring with NH$_2$ and SCH$_3$ substituents] | Compound 8 described in JP-A-2-91061 |
| (B) [structure: 2,6-dichloro-4-trifluoromethylphenyl group attached to N-N ring with NH$_2$ and SOCH$_3$ substituents] | Compound 175 described in JP-A-1-230562 |
| (C) [structure: 2,6-dichloro-4-trifluoromethylphenyl group attached to N-N ring with NH$_2$ and SO$_2$CH$_3$ substituents] | Compound 40 described in JP-A-2-91061 |
| (D) [structure: imidacloprid] | imidacloprid |

TEST EXAMPLE 1

Acetone solution (1 μl) containing 0.2 μg of each test compound was applied to the lower side of thorax of female adult German cockroach (*Blattella germanica*), to which a feed (solid feed for breeding of rats manufactured by Oriental Yeast Co., Ltd.) and water were given. After 7 days from the application of the test compound, the number of dead insects was checked and a mortality was obtained. (Replication of three times for one group consisting of 10 insects). The results are shown in Table 4.

TABLE 4

| Compound No. | Mortality (%) | Compound No. | Mortality (%) |
|---|---|---|---|
| (1) | 100 | (43) | 100 |
| (2) | 100 | (44) | 100 |
| (3) | 100 | (45) | 100 |
| (7) | 100 | (46) | 100 |
| (9) | 100 | (47) | 100 |
| (10) | 100 | (48) | 100 |
| (11) | 100 | (49) | 100 |
| (13) | 100 | (51) | 100 |
| (14) | 100 | (52) | 100 |
| (18) | 100 | (53) | 100 |
| (19) | 100 | (54) | 100 |
| (20) | 100 | (56) | 100 |
| (21) | 100 | (58) | 100 |
| (22) | 100 | (59) | 100 |
| (23) | 100 | (60) | 100 |
| (24) | 100 | (61) | 100 |
| (31) | 100 | (62) | 100 |
| (32) | 100 | (63) | 100 |
| (34) | 100 | (66) | 100 |
| (36) | 100 | (67) | 100 |
| (39) | 100 | (A) | 3.3 |
| (41) | 100 | (B) | 3.3 |
|  |  | (B) | 23 |

TEST EXAMPLE 2

The bottom of a polyethylene cup of 5.5 cm in diameter was covered with a filter paper of the same size, and 0.7 ml of a 1:200 dilution (500 ppm) with water of the emulsifiable concentrate of each test compound obtained in accordance with Formulation Example 1 was dripped onto the above filter paper and 30 mg of sucrose as feed was uniformly placed in the cup. Ten female adult house flies (*Musca domestica*) were put in the cup and the cup was covered. After 24 hours, the number of the dead insects was checked and a mortality was obtained. The results are shown in Table 5.

TABLE 5

| Compound No. | Mortality (%) | Compound No. | Mortality (%) |
|---|---|---|---|
| (1) | 100 | (32) | 100 |
| (2) | 100 | (33) | 100 |
| (4) | 100 | (34) | 100 |
| (5) | 100 | (35) | 100 |
| (6) | 100 | (36) | 100 |
| (7) | 100 | (37) | 100 |
| (8) | 100 | (38) | 100 |
| (10) | 100 | (39) | 100 |
| (11) | 100 | (41) | 100 |
| (12) | 100 | (42) | 100 |
| (13) | 100 | (43) | 100 |
| (14) | 100 | (44) | 100 |
| (15) | 100 | (45) | 90 |
| (16) | 100 | (46) | 100 |
| (17) | 100 | (47) | 100 |
| (18) | 100 | (48) | 100 |
| (20) | 100 | (49) | 100 |
| (22) | 100 | (51) | 100 |
| (24) | 100 | (52) | 100 |

TABLE 5-continued

| Compound No. | Mortality (%) | Compound No. | Mortality (%) |
|---|---|---|---|
| (26) | 100 | (55) | 100 |
| (27) | 100 | (61) | 100 |
| (28) | 100 | (62) | 100 |
| (29) | 100 | (69) | 100 |
| (30) | 100 | (A) | 0 |
| (31) | 100 | (B) | 50 |
|  |  | (C) | 10 |

TEST EXAMPLE 3

Rice seeds (var.: Nipponbare) were sown in the sandy loam filled in a plastic cup of 90 ml. After raising for 20 days in a greenhouse, the seedlings were sprayed with 40 ml (for one seedling) of a dilution (a given concentration) with water of emulsifiable concentrate of each test compound obtained in accordance with Formulation Example 1. After air drying the sprayed solution, the seedlings were transferred to a plastic case, in which twenty larvae of first instar of brown rice planthopper (*Nilaparvata lugens*) were put, and the case was covered and kept in a greenhouse at 27° C. for 6 days. Thereafter, the mortality was checked and the control effect was judged by the following criteria. The results are shown in Table 6.

| Control effect | Mortality |
|---|---|
| 4 | 100 |
| 3 | 90–99 |
| 2 | 60–89 |
| 1 | 30–59 |
| 0 | 0–29 |

TABLE 6

| Test compound | Concentration (ppm) | Control effect | Test compound | Concentration (ppm) | Control effect |
|---|---|---|---|---|---|
| (1) | 12.5 | 4 | (34) | 12.5 | 4 |
| (2) | 12.5 | 4 | (35) | 12.5 | 4 |
| (4) | 12.5 | 4 | (36) | 12.5 | 4 |
| (10) | 12.5 | 4 | (37) | 12.5 | 4 |
| (7) | 12.5 | 4 | (38) | 12.5 | 4 |
| (11) | 12.5 | 4 | (41) | 12.5 | 4 |
| (13) | 12.5 | 4 | (42) | 12.5 | 4 |
| (14) | 12.5 | 4 | (43) | 12.5 | 4 |
| (15) | 12.5 | 4 | (46) | 12.5 | 4 |
| (18) | 12.5 | 4 | (47) | 12.5 | 4 |
| (20) | 12.5 | 4 | (48) | 12.5 | 4 |
| (22) | 12.5 | 4 | (49) | 12.5 | 4 |
| (24) | 12.5 | 4 | (51) | 12.5 | 4 |
| (26) | 12.5 | 4 | (52) | 12.5 | 4 |
| (27) | 12.5 | 4 | (56) | 12.5 | 3 |
| (28) | 12.5 | 4 | (61) | 12.5 | 4 |
| (29) | 12.5 | 3 | (62) | 12.5 | 4 |
| (30) | 12.5 | 4 | (A) | 12.5 | 2 |
| (31) | 12.5 | 4 | (B) | 12.5 | 2 |
| (32) | 12.5 | 4 | (C) | 12.5 | 1 |
| (33) | 12.5 | 4 |  |  |  |

TEST EXAMPLE 4

The bottom of a polyethylene cup of 5.5 cm in diameter was covered with a filter paper of the same size, and 1 ml of a dilution (50 ppm) with water of the emulsifiable concentrate of each test compound obtained in accordance with Formulation Example 1 was dripped onto the filter paper. After the diluted emulsifiable concentrate spread all over the surface of the filter paper, one grain of maize seed having a root of about 2 cm was placed thereon, and about thirty eggs of southern corn rootworm (*Diabrotica undecimpunctata howardi*) were placed about 3 cm apart from the seed. They were kept at 28° C. for 8 days and, then, the control effect was evaluated in accordance with the criteria given in Test Example 3. The results are shown in Table 7.

TABLE 7

| Test compound | Control effect | Test compound | Control effect |
|---|---|---|---|
| (1) | 4 | (32) | 4 |
| (2) | 4 | (33) | 4 |
| (4) | 4 | (34) | 4 |
| (5) | 4 | (35) | 4 |
| (6) | 4 | (36) | 4 |
| (7) | 4 | (37) | A |
| (8) | 4 | (38) | 4 |
| (9) | 4 | (39) | 4 |
| (10) | 4 | (41) | 4 |
| (11) | 4 | (42) | 4 |
| (12) | 4 | (43) | 4 |
| (13) | 3 | (44) | 4 |
| (14) | 4 | (45) | 4 |
| (15) | 4 | (46) | 4 |
| (16) | 4 | (47) | 4 |
| (17) | 3 | (48) | 4 |
| (18) | 4 | (50) | 4 |
| (20) | 4 | (51) | 3 |
| (22) | 4 | (52) | 4 |
| (24) | 4 | (55) | 4 |
| (26) | 4 | (56) | 4 |
| (27) | 4 | (61) | 4 |
| (28) | 4 | (62) | 4 |
| (29) | 4 | (69) | 4 |
| (30) | 4 | (A) | 0 |
| (31) | 4 | (B) | 0 |
|  |  | (C) | 0 |

TEST EXAMPLE 5

An acetone solution of the test compound was added to a mite feed medium at a given concentration, followed by uniformly mixing them. Thereto was further added an equal amount of a mite feed medium and they were further uniformly mixed. The number of mites in the medium after mixing was about 300–500/1 g. The medium was stored for 4 weeks at a constant temperature (25° C.) and a constant humidity (75%RH for *Tyrophagus putrescentiae* and 65%RH for *Dermatophagoides farinae*). Thereafter, the number of surviving mites in a given amount of the medium was counted and a multiplication inhibiting rate was obtained by the following formula.

Multiplication inhibiting rate =

$$\frac{\text{The number of surviving mites in the untreated medium} - \text{the number of surviving mites in the treated medium}}{\text{The number of surviving mites in the untreated medium}} \times 100$$

As a result, the compound (2) at a concentration of 300 ppm (final concentration) showed a multiplication inhibiting rate of 100% for *Tyrophagus putrescentiae* and *Dermatophagoides farinae*.

The compounds (6), (11), (15), (23), (24), (27), (32), (34), (39), (41), (47) at a same concentration showed more than 80% multiplication inhibiting rate for *Dermatophagoides farinae*.

TEST EXAMPLE 6

Rice seedlings (2.5 leaf stage) planted in a nursery box were applied with a test compound formulated in accordance with the formulation example 3, or the compound (D) of commercial granule formulation sold as Admire® 2G in Japan. On the next day of treatment, rice seedlings were transplanted into a paddy field with the plot size of 6 by 7 meter for each treatment. One hundred twenty adult *Nilaparvata lugens* were released onto a rice plant of each treatment plot after 23, 30 and 64 days of treatment. At the designated days after treatment, number of live insects (N. lugens) on the rice plant on which N. lugens were released and four surrounding plants were counted. The results are shown in Table 8.

TABLE 8

| Test Compound | Rate | Number of live insects/2 reps (10 plants) | | | |
|---|---|---|---|---|---|
| | | +57 | +71 | +91 | +105 |
| | | days after treatment | | | |
| (1) | 1 g ai/box* | 3 | 17 | 16 | 84 |
| (D) | 2 g ai/box | 1 | 63 | 25 | 167 |
| untreated | — | 35 | 81 | 193 | 848 |

*nursery box

TEST EXAMPLE 7

Rice seeds were sprayed with a test compound or the compound (D) formulated in accordance with the formulation example 1. The treated seeds were then planted in nursery boxes. The rice seedlings at 2.5 leaf stage were transplanted into a paddy field with the plot size of 6 by 7 meter for each treatment after 34 days of treatment. At the designated days after the transplanting, number of adult *Lissorhoptrus oryzophilus* which naturally occurred in field was counted on 50 rice plants from each plot. The results are shown in Table 9.

TABLE 9

| Test Compound | Rate | Number of live adults/3 reps (150 plants) | | |
|---|---|---|---|---|
| | | +6 | +13 | +20 |
| | | days after transplanted | | |
| (1) | 100 g ai/ 100 kg Seed | 11 | 10 | 6 |
| (D) | 100 g ai/ 100 kg Seed | 26 | 14 | 27 |
| untreated | — | 18 | 26 | 43 |

What is claimed is:

1. A triazole compound represented by the following formula:

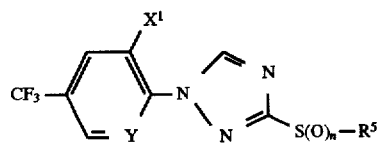

wherein $R^1$ represents a hydrogen atom, a lower alkyl group, a halogen atom, a 1-pyrrolyl group, a group represented by the formla $NR^2R^3$, wherein $R^2$ and $R^3$ are the same or different and each represent a hydrogen atom, an alkyl group, a cycloalkyl group, an alkoxyalkyl group, a alkylthioalkyl group, and alkylthiocarbonyl group, an alkoxycarbonylsulfenyl group, and alkylthio group, an alkylsulfonyl group, a substituted phenyl group, an alkoxycarbonyl group, an unsubstituted or alkoxy-substituted alkanoyl group, a saturated heterocyclic ring, or the formula:

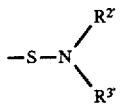

wherein $R^{2'}$ and $R^{3'}$ are the same or different and each represent an alkyl group, an alkoxycarbonyl group, an alkoxycarbonyl-substituted alkyl group, or $R^{2'}$ and $R^{3'}$ link to each other to form an oxygen-containing alkylene group, or $R^2$ and $R^3$ link to each other to form an unsubstituted or substituted nitrogen-containing saturated heterocyclic ring represented by $NR^2R^3$ or a group represented by the formula $N=CR^4R^6$, wherein $R^4$ represents a hydrogen atom, an alkyl group or an unsubstituted or substituted phenyl group and $R^6$ represents a hydrogen atom, an alkyl group, an alkoxy group or a dialkylamino group; $R^5$ represents a methyl group substituted with at least one halogen atom or an ethyl group substituted with at least one halogen atom; n represents 0, 1 or 2; Y represents a nitrogen atom or a group represented by the formula $CX^2$, wherein $X^2$ is as defined hereinafter; and $X^1$ and $X^2$ are the same or different and each represents a halogen atom, a nitro group or a cyano group.

2. A triazole compound according to claim 1, wherein $R^5$ is a group represented by the formula $CF_2Z$ where Z represents a halogen atom, a hydrogen atom, a methyl group, a difluoromethyl group, a trifluoromethyl group or a bromodifluoromethyl group.

3. A triazole compound according to claim 1, wherein $R^5$ is a trifluoromethyl group, a difluoromethyl group, a chlorodifluoromethyl group, a bromodifluoromethyl group, a 1,1,2,2-tetrafluoroethyl group, a 2,2,2-trifluoroethyl group, a pentafluoroethyl group, a 1,1-difluoroethyl group or a 2-bromo-1,1,2,2-tetrafluoroethyl group.

4. A triazole compound according to claim 1, wherein $R^5$ is a trifluoromethyl group.

5. A triazole compound according to claim 1, wherein the saturated heterocyclic ring represented by $R^2$ or $R^3$ is 2-tetrahydropyranyl group.

6. A triazole compound according to claim 1, wherein the substituent of the substituted saturated heterocyclic ring represented by $NR^2R^3$ is at least one member selected from the group consisting of alkyl group, halogen atom, alkoxy group, hydroxyl group, mercapto group, alkoxycarbonyl group, oxo group and acyloxy group.

7. A triazole compound according to claim 1, wherein the unsubstituted or substituted saturated heterocyclic ring represented by $NR^2R^3$ is one selected from the group consisting of aziridine ring, azetidine ring, pyrrolidine ring, morpholine ring, thiomorpholine ring, isothiazolidine ring, 1,3-oxazolidine ring and 1,3-thiazolidine ring.

8. A triazole compound according to claim 1, wherein the substituent in the substituted phenyl group represented by $R^4$ is at least one member selected from the group consisting of hydroxyl group, alkoxy group, alkyl group, nitro group, halogen atom, phenyl group, phenoxy group, alkylthio group, amino group, carboxyl group, cyano group, alkoxycarbonyl group and acyloxy group.

9. A triazole compound according to claim 1, wherein $R^1$ is a hydrogen atom, a methyl group or a group represented by the formula $NR^2R^3$.

10. A triazole compound according to claim 9, wherein $R^2$ is a hydrogen atom, an alkanoyl group or an alkoxycarbonyl group and $R^3$ is a hydrogen atom, an alkyl group, a cycloalkyl group, an alkoxycarbonyl group, an alkoxycarbonylsulfenyl group, an alkoxyalkyl group or the formula

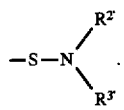

11. A triazole compound according to claim 1, wherein Y is a group represented by the formula $CX^2$.

12. A triazole compound according to claim 1, wherein n is 0.

13. A triazole compound according to claim 1, wherein $R^1$ is a hydrogen atom, a methyl group or a group represented by the formula $NR^2R^3$, $R^2$ is a hydrogen atom, $R^3$ is a hydrogen atom, an alkyl group, a cycloalkyl group or an alkoxyalkyl group, Y is a group represented by the formula $CX^2$, and n is 0.

14. An insecticide or acaricide containing the triazole compound of claim 1 as an active ingredient.

15. A method for controlling insects and mites which comprises applying an effective amount of the triazole compound of claim 1 to a locus where insects and mites or insects or mites inhabit.

16. A triazole compound according to claim 1, wherein $R^1$ is a hydrogen atom, a lower alkyl group, a group represented by the formula $NR^2R^3$; wherein $R^2$ and $R^3$ are the same or different and are a hydrogen atom or an alkyl group or $R^1$ is a group represented by the formula $N=CHR^4$, wherein $R^4$ is an unsubstituted or substituted phenyl group; and $R^5$ is a methyl group substituted with at least one halogen atom.

* * * * *

UNITED STATES PATENT AND TRADEMARK OFFICE
CERTIFICATE OF CORRECTION

PATENT NO. : 5,756,522
DATED : May 26, 1998
INVENTOR(S) : Hiroki TOMIOKA et al.

It is certified that error appears in the above-identified patent and that said Letters Patent is hereby corrected as shown below:

Correct the formula in the Abstract and in claim 1 at column 40, line 60 to include the --$R^1$-- group as follows:

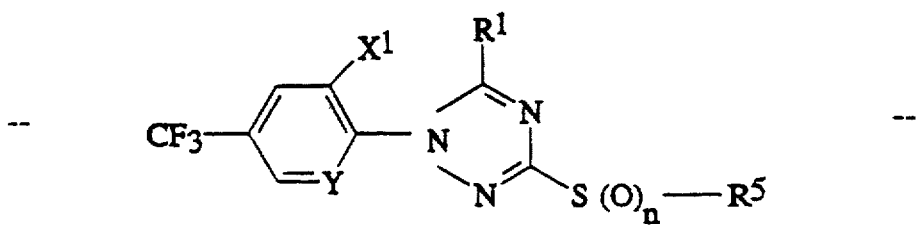

Signed and Sealed this

Sixteenth Day of February, 1999

Attest:

Attesting Officer

*Acting Commissioner of Patents and Trademarks*